United States Patent
Wu et al.

(12)

(10) Patent No.: US 6,290,959 B1
(45) Date of Patent: *Sep. 18, 2001

(54) METHOD FOR SCREENING COMPOUNDS FOR INHIBITING BACTERIAL ATTACHMENT TO HOST CELL RECEPTORS

(75) Inventors: Xue-Ru Wu, Woodside; Tung-Tien Sun, Scarsdale, both of NY (US)

(73) Assignee: New York University, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 35 days.

(21) Appl. No.: 08/957,130

(22) Filed: Oct. 24, 1997

Related U.S. Application Data

(60) Provisional application No. 60/029,762, filed on Oct. 24, 1996, now abandoned.

(51) Int. Cl.[7] .............................. A61K 39/40; C12Q 1/68; C12Q 1/04; G01N 33/53

(52) U.S. Cl. ..................................... 424/150.1; 424/152.1; 435/7.3; 435/34; 435/69.7; 435/235.1; 435/6; 435/320.1; 536/23.7

(58) Field of Search .............................. 435/7.3, 34, 69.7, 435/235.1, 320.1, 6; 424/150.1, 152.1; 536/23.7

(56) References Cited

U.S. PATENT DOCUMENTS

| | | | |
|---|---|---|---|
| 5,486,454 | * | 1/1996 | Madonna et al. .................... 435/6 |
| 5,510,241 | * | 4/1996 | Thorns .............................. 435/7.3 |
| 5,635,617 | * | 6/1997 | Doran et al. ...................... 536/23.7 |

OTHER PUBLICATIONS

Xue–Ru et al. 1994. Mammalian Uroplakins. J. of Biol. Chem. 269 (18): 13716–13724.*

Xue–Ru et al. 1995. Selective Interactions of UPIa and UPIb, Two Members of the Transmembrane 4 Superfamily, with Distinct Single Transmembrane–domained Proteins Differentiated Urothelial Cells. J. of Biol. Chem. 270 (50): 29752–29759.*

Yu et al. 1990. Uroplakin I: A 27–kD Protein Associated with the Asymmetric Unit Membrane of Mammalian Urothelium. 111:1207–1216.*

Muchmore et al. 1985. Uromodulin: A Unique 85–Kilodalton Immunosuppressive Glycoprotein Isolated from Urine of Pregnant Women. Science. 229: 479–481.*

Thorns et al. 1990. Detection of a Novel Fimbrial Structure on the Surface of Salmonella enteritidis by Using a Monoclonal Antibody. J. of Clin. Micro. 28 (11): 2409–2414.*

Sherblom et al. 1988. The Lectin–like Interaction between Recombinant Tumor Necrosis Factor and Uromodulin. J. of Biol. chem. 263 (11): 5418–5424.*

Xue–Ru et al. 1990. Large Scale Purification and Immunolocalization of Bovine Uroplakins I, II and III. 265 (31) pp. 19170–19179.*

\* cited by examiner

Primary Examiner—Jennifer E. Graser
Assistant Examiner—Ja-Na A. Hines
(74) Attorney, Agent, or Firm—Browdy and Neimark

(57) ABSTRACT

Uroplakins Ia and Ib are the major urothelial receptors of type 1 fimbriated microorganisms. These uroplakins are used to screen compounds for treating urinary tract infections by testing if the compounds inhibit bacterial adhesion to the uroplakins. Additionally, compounds which inhibit adhesion of microorganisms expressing type 1 fimbriae, such as Tamm-Horsfall protein, are used to treat or inhibit infection by these microorganisms.

5 Claims, 9 Drawing Sheets

FIG. 6A

Primary Data:

Deduced Sequences:

1 C1 and C2     D-(E)-V-?-F-T-S-A-F-R-A-T-T-P-E-V-V-F-P-
                                                        1

2 C1 only       L-T-F-Y-S-A-D-S-N-Q-G-I-

3 C2 only       I-(W)-Q-E-?-?-G-

4 T1, T2 and #2 Q-M-L-T-F-Y-S-A-D-S-N-Q-G-
                                          2

5 T1 only       D-Y-M-V-S-N-P-S-L-I-T-K

6 T2 only       L-G-H-L-D-Y-L-F-T-K
                                    3

FIG. 7A

```
  1                                                         GGCAGAGAAGGCAGGACT
 19 ATGGCTTCTGCAGCAGCAGCAACGACAGAGAAGGGGTCTCCAGTTGTGGTGGGTCTGCTGGTCATGGGCAACATC
  1 M  A  S  A  A  A  A  T  T  E  K  G  S  P

94 ATTATTCTGCTGTCAGGCCTGGCCCTGTTTGCTGAAACGGTATGGGTGACCGCTGACCAGTACCGCATATACCCG
 26                                            W  V  T  A  D  Q  Y  R  I  Y  P

169 CTGATGGGCGTCTCGGGCAAGGATGACGTCTTCGCCGGCGCCTGGATCGCCATCTTCTGCGGCTTCTCCTTCTTC
 51 L  M  G  V  S  G  K  D  D

244 GTGGTGGCCAGCTTTGTGTGGGCGCAGCACTCTGCCGCCGCCGCTCCATGATCCTCACGTACCTGATACTCATG
 76                                C  R  R  R  S

319 CTCATCATCTACATCTTTGAGTGCGCCTCCTGCATCACGTCCTACACCCACCGAGACTATATGGTGTCCAACCCG
101                                           T  S  Y  T  H  R  D  Y  M  V  S  N  P
                                                              ↳5

394 TCCCTGATCACCAAGCAGATGTTGACATTCTATAGTGCAGACTCGAACCAGGGCCGGGAACTGACCCGCCTCTGG
126 S  L  I  T  K  Q  M  L  T  F  Y  S  A  D  S  N  Q  G  R  E  L  T  R  L  W
         ↳4    ↳2

469 GATCGCATCATGATTGAGCAAGAGTGCTGTGGCACGTCAGGCCCCATGGACTGGGTGAACTTCACGTCTGCCTTC
151 D  R  I  M  I  E  Q  E  C  C  G  T  S  G  P  M  D  W  V  Ⓝ  F  T  S  A  F
         ↳3                                                    ↳1

544 CGGGCCACCACCCCAGAGGTGGTGTTCCCCTGGCCCCCGCTATGCTGTCGACGGACCGGCAACTTCATCCCAGTC
176 R  A  T  T  P  E  V  V  F  P  W  P  P  L  C  C  R  R  T  G  N  F  I  P  V

619 AATGAAGAAGGCTGCCGCCTGGGCCACCTGGACTACCTGTTCACCAAGGGCTGCTTTGAACATATTGGCCACGCC
201 N  E  E  G  C  R  L  G  H  L  D  Y  L  F  T  K  G  C  F  E  H  I  G  H  A
                    ↳6
```

FIG. 7B

```
 694 ATCGACAGCTACACGTGGGGCATCTCGTGGTTTGGGTTTGCCATCCTGATGTGGACGCTCCCCGTGATGCTGATA
 226  I   D   S   Y   T   W   G
 769 GCCATGTATTTCTACACCACGTTGTGAGAACGAGAAGTGAAGGCCACGTGCACACCTGGCTTCCTCCTCCTCCTG
 251                 Y   T   T   L   *
 844 CTCTGGCTTCCTCTGGCTGAGATGGCCGACTCGCCTCTCCCTGTCCCACCTCCCTGGCCCAGTCCTCCCTCCACT
 919 CCAAAGATGTTTTACCAGGTTTCTGAGCCCTGCTGAGAGTCGGGGTGCCCTAAAACCCCTGGACATCCTCTTACT
 994 AAGGACTAAGCTTCCAGCAAATTCTCTAAGGGGTGTGTAGCATGTGTGTACAGACCGTTAGTCCTTAACCTCCTT
1069 TCACTAGACTGATTCTTGGCCCATCTTTCAGGGTCAACTTCAAGTCCTGTCCTCGGGGGGCCCTTTCCTGATCT
1144 CACCACCCCATTCACAGATGCCTTTCTTATAGTTCCCAGAGCTCCTCCTCCATGGTGGATGTCATCATCATCACT
1219 GAATAGTTTGTGATTGTCTGTTTAAATTCTGGTAGAACTGGGATTGCCATGAGGAGAGGGACAAGTTCTGTTATG
1294 GTCACTTTAACATCCCTGCATCACCTGGCATGGGCTGAGCACGGACATTCAATAAATACTACTTGAATG(A)n
```

FIG. 8A

```
  1 GCGTGCAGAGAGCCGACACAGTACCAGGAGGAGGAGGAGAGGCTTGGGGAAATCCTGAAG
 62 ATGGCCAAAGACGACTCCACTGTTCGTTGCTTCCAGGGCCTGCTGATTTTTGGAAATGTGATTATCGGTATGTGC
  1  M  A  K  D  D  S  T  V  R  C

137 AGCATCGCCCTGATGGCAGAGTGCATCTTCTTTGTATCAGACCAAAACAGCCTCTACCCACTGCTTGAAGCCACC
 26                                        S  D  Q  N  S  L  Y  P  L  L  E  A  T

212 AACAATGACGACATCTATGCGGCAGCCTGGATTGGCATGTCTGTTGGCATCTGCCTCTTCTGCCTCTCTGTCCTG
 51  N  N  D  D

287 GGCATCGTAGGCATCATGAAGTCCAACAGGAAAATTCTTCTGGTGTATTTCATCCTGATGTTTATTGTATATGCT
 76                    K  S  N  R  K

362 TTTGAAGTGGCATCTTGTATCACAGCAGCAACACAACGAGACTTTTTCACACCCAACCTCTTCCTGAAGCAGATG
101                                        Q  R  D  F  F  T  P  N  L  F  L  K  Q  M

437 CTGGAGAGATACCAAAACAACAGTCCTCCAAACAATGATGACCAATGGAAAAACAATGGAGTCACCAAGACCTGG
126  L  E  R  Y  Q (N) N  S  P  P  N  N  D  D  Q  W  K  N  N  G  V  T  K  T  W

512 GACAGACTTATGCTCCAGGACAATTGCTGTGGTGTAAATGGCCCGTCAGACTGGCAGAAATACACCTCTGCCTTC
153  D  R  L  M  L  Q  D  N  C  C  G  V  N  G  P  S  D  W  Q  K  Y  T  S  A  F

587 CGGACTGAGAACAGCGATGCTGACTACCCCTGGCCTCGTCAATGCTGTGTTATGAACAGCCTGAAAGAACCTCTC
176  R  T  E  N  S  D  A  D  Y  P  W  P  R  Q  C  C  V  M  N  S  L  K  E  P  L

662 AACCTGGACGCCTGCAAATTAGGAGTGCCTGGATACTACCATAGTCATGGCTGCTATGAGCTCATCTCTGGACCA
201  N  L  D  A  C  K  L  G  V  P  G  Y  Y  H  S  H  G  C  Y  E  L  I  S  G  P

737 ATGAACCGACATGCCTGGGGAGTTGCATGGTTTGGATTTGCCATCTCTGTTGGACTTTCTGGTTCTCCTGGGT
226  M  N  R  H  A  W  G

812 ACCATGTTCTACTGGAGCAGAATTGACTATTAAGAATGAAGTGTATGCACCATACCACTCGCCACAGTGACTTTG
251              Y  W  S  R  I  D  Y  *
```

FIG. 8B

```
 887 GATTTGGTGCTGGAAATGCTGTCTCCTAATGTTCTACCTTTGTGCTGCTGCCCGGGAACTTACGCATTCTTCCTACAT
 962 TGCCAAGTACGTTGGTATGGGGTTCCTTTAAGACTCTCAGACTCTGAAATTTCAGCACATGTGTTTTCACCCTGA
1037 TCTAGGATTCTGCAACATTGTTATAGACTGTAGGAAGGGAGGATTTAGGATAGTAGATAATAACTATTCCCATC
1112 TTTGTTTATTTTAATGTGGGGGCATAAAGACATTCCTAGGAACCTGTGTTATACTGCAAGCCAAGTCTGTATTG
1187 GGACAGCAAATCTGCCTGTATTCTCACTGCTTTCTAAAAGTACCCTGATGGCACCCCACTCCAGTACTCTTGCC
1262 TGGAAATCCCATGGACGGAGACCTGATGGGCTGCAGTCCATGGGGTCGCAAAGAGTCGGACCCGACTGGGCG
1337 ACTTCACTTTCACTTTCATGCATTGGAGAAGGAAATGCAACCCACTCCAGTGTTCTTGCCTGAAGCGACTTAG
1412 TCCCAGGGATGGAGGAGCCTGGAGGGCTGCCGTCTATGGGGTCACACAGAGTCGGACACGAGAAGACTGAAGCGACTTAG
1487 CAGCAGCAGCAGCAAAGGCTTTCATTGTATCAGTATTGTCCCAGTGAAGTGATTCTCTTAAAGCTAGCTTGGGAACCTT
1562 TCTTTTGAATTTGTTCTATGGTGGCTCCCACCTCAAGTACAGACTCAAGTGGTTGAAATTTCCTCTCAGACACTGCAGAGTAATTCAT
1637 TATTATCCAAGACAAGGCCTGATCTTGAACAAACAGTACGTGAACTTTGGGACAAAGGAGACCTGTTACACATTT
1712 GCTGGTAACCTCAATTCTCCCACTAATTAAAAGTACGTGAACTTTGGGACAAAGGAGACCTGTTACACATTT
1787 ACCACCTTCAACCTAAAAACTGCTTTCCTTCTGATCTGTTTCCTTTTGTGATCCTGAAGGAATTTCTTATAACACATTTG
1862 TGTGCACTGCAAAATATTTTTCCTTCTGATCTGTTTCCTTTTGTGATCCTGAAGGAATTTCTTATAACACATTTG
1937 TCTTTATATAAATAAAGAGAGTTTTAAAT(A)n
```

METHOD FOR SCREENING COMPOUNDS FOR INHIBITING BACTERIAL ATTACHMENT TO HOST CELL RECEPTORS

CROSS-REFERENCE TO RELATED APPLICATIONS

The present application claims priority under 35 U.S.C. § 119(e) from U.S. provisional application Ser. No. 60/029,762, filed Oct. 24, 1996, now abandoned.

FIELD OF THE INVENTION

The present invention is directed to a method for identifying compounds for their efficacy in inhibiting bacterial infections of the urinary tract. This application is based upon provisional application Ser. No. 60/029,762, the entire contents of which are hereby incorporated.

BACKGROUND OF THE INVENTION

Type 1 fimbriae promote microbial adherence to a variety of mammalian cells and are thought to play an important role in the establishment of various infections. These type 1 fimbriae have mannose-specific adhesins, which enable these microorganisms to infect an organism. To facilitate the attachment to eukaryotic receptors, microorganisms bearing type 1 fimbriae assemble these fimbriae to present at their tips adhesin molecules (Hanson et al., 1998; Jones et al., 1995; Kuehn et al., 1992). Two major classes of fimbriae have been functionally defined in uropathogenic E. coli that can account for over 90% of the urinary tract infections. P fimbriae are expressed in about 70% of urinary tract isolates, particularly those from pyelonephritis patients, and they bind to the galactose-alpha(1,4)-galactose portion of the glycolipid receptors of the kidney (Johnson et al., 1992; O'Hanley et al., 1985; Stromberg et al., 1990; Stromberg et al., 1991). The type 1 fimbriae are expressed by over 90% of the uropathogenic E. coli, and they can bind, via mannose moieties, to the urothelial surface (Lin et al., 1995; Hutgren et al., 1985; O'Hanley et al., 1985; Sater et al., 1993; Schaeffer, 1991; Venegas et al., 1995). Immunohistochemical staining of voided urothelial cells of urinary tract infection patients showed adhering E. coli with type 1 fimbriae (Fujita et al., 1989; Kisielius et al., 1989).

Animal studies showed that E. coli expressing type 1 fimbriae, but not those harboring mutated ones, can cause urinary tract infection. These results clearly establish the functional importance of the mannose-sensitive, type 1 fimbriae in urinary tract infections (Iwahi et al., 1983; Keith et al., 1986; Schaeffer et al., 1987; Johanson et al., 1992). Virtually nothing is known, however, about the receptors that presumably bear the mannoses that are recognized by type 1 fimbriae. Consequently, the precise role of this kind of fimbriae and their functional relationship with the P fimbriae in various types of infections heretofore have not been well understood (Eisenstein, 1989; Falkow et al., 1992; Hopelmann and Tuamanen, 1992; Hultgren et al., 1993; Schoolnik et al., 1987; Stamm et al., 1989).

Many microorganisms express type 1 fimbriae, which accounts for their infectious nature. Among these microorganisms are Salmonella, Klebsiella, Citrobacter, Shigella, Enterobacter, Serratia, Proteus, Morganella, and Providencia.

Urinary tract infections are among the most common infectious diseases, accounting for almost five million cases annually and causing considerable morbidity and mortality (Schaeffer, 1994; Schoolnik, 1989; Stamm et al., 1989). Increasing incidence of antibiotics-resistant E. coli, which cause a great majority (up to 95%) of these infections, calls for additional therapeutic considerations. One useful approach entails the inhibition of bacterial attachment to the urothelial surface, which is a crucial initial event involving the precise interaction between a group of bacterial adhesive molecules, called adhesins, and their cognate urinary tract receptors (Falkow et al., 1992; Hopelman and Tuomanen, 1992; Hultgren et al., 1993; Schaeffer, 1988; Schoolnik et al., 1987; Stamm et al., 1989). Knowledge of the molecular details of the receptor:adhesin interface may provide a basis for rational drug design for preventing and treating a variety of infections.

Adhesion of causative bacteria to host urothelial surface depends on three principal factors: the expression of proper bacterial adhesins, the availability of host receptors, and the functional status of an innate host defense mechanism.

Pharmaceutical agents which prevent attachment of bacterial pathogens to particular receptors on the host cells' membranes would cause little interference with normal host function, since they would act only on the attachment of the pathogens to receptors. The bacteria would survive and continue to grow, but would be more susceptible to elimination by host defenses including the flushing action produced by urine flow. Counteraction of infection by interfering with or preventing attachment of type 1 fimbriae to host cells' membranes would be less likely to result in selection for drug resistance because the anti-adhesin compounds involved need not favor the growth of mutants that are resistant to their action. In other words, compounds which interfere with or prevent attachment to host cells' receptors do not affect bacterial growth, so there is no favoring of mutants which are resistant to the action of these compounds.

Asymmetric unit membrane (AUM), a highly specialized membrane, covers the bulk of the urinary tract and performs two functions: it serves as a physically stable and yet flexible permeability barrier against urine and provides a vehicle for the reversible adjustment of the bladder surface area by incorporating AUM-containing cytoplasmic vesicles to the luminal surface during bladder expansion and by retrieving the AUM back into the cytoplasm during bladder contractions. However, how AUM performs these functions is unclear.

Significant progress has recently been made to characterize biochemically the apical surface of mammalian urothelium, which is covered with numerous rigid-appearing 0.3–0.5 micron plaques. In cross-sections, the luminal leaflet of the plaque membrane is twice as thick as the cytoplasmic leaflet, hence the term "asymmetrical unit membrane". Urothelial asymmetrical unit membranes have recently been found to contain four major integral membrane proteins, which have been named uroplakin Ia, 27 kDa; uroplakin Ib, 28 kDa; uroplakin II, 15 kDa; and uroplakin III, 47 kDa. (Lin et al., 1994; Lin et al., 1995; Walz et al., 1995; Wu et al., 1994; Wu et al., 1990; Wu and Sun, 1993; Yu et al., 1994; Yu et al., 1990).

All of the major asymmetrical unit membrane proteins have dominant luminal domains with relatively little or, in the cases of uroplakin I proteins and uroplakin II, almost no cytoplasmic domains. The asymmetrical distribution of the uroplakin domains across the lipid bilayer suggests that the luminal domains may interact to form the 16-nm protein particles protruding luminally and may explain why the luminal leaflet is thicker than its cytoplasmic leaflet. Ultrastructural localization confirmed that the uroplakins are associated with the asymmetrical unit membrane plaques in situ. Because these plaques occupy 70–80% of the urothelial apical surface and are only interrupted by short interplaque "hinge" areas, these four uroplakins, as the major asymmetrical unit membrane subunits, are the predominant protein components of the urothelial apical surface.

Together, the four uroplakins form 16-nm luminal protein particles that are arranged in two-dimensional crystalline arrays. Image processing revealed that each 16-nm particle consists of six inner and six outer domains interconnected, forming a continuous strand in the shape of a twisted ribbon (Waltz et al., JMB, 1995). cDNA cloning showed that uroplakins Ia and Ib are closely related isoforms, sharing 39% amino acid sequences; they belong to a family of cell surface proteins having four conserved transmembrane domains (Yu et al., JCB, 1995). Uroplakins II (UPII) and III (UPIII) have a single transmembrane domain located near the C-terminus (Wu, JCS, 1994; Lin, JBC, 1995). In a nearest-neighbor analysis using chemical cross linking, it has been demonstrated that uroplakins Ia (UPIa) and Ib (UPIb) can be cross-linked to uroplakins II and III, respectively, raising the possibility that two types of 16-nm particles exist and that each contains two related pairs of uroplakins (Wu, JBC, 1995).

Although it has long been hypothesized that type 1 fimbriated microorganisms bind to the urothelial surface and that this binding plays a major role in infections such as urinary tract infections, the receptors have not heretofore been identified. Consequently, little is known about the details of this bacterial fimbriae:urothelial receptor binding. Also, it was impossible to design simple and physiologically relevant screening for drugs that can interfere with this binding. Identification of urothelial receptors will solve these problems.

While yeast or intestinal epithelial cells have been traditionally used to screen drugs for efficacy in treating urinary tract infections, there is no assurance that bacterial adhesion to yeast or to intestinal epithelial cells is the same as bacterial adhesion to epithelial cells in the urinary tract. It is not known if the type 1 fimbriated microorganisms bind to a protein backbone as well as to mannose, which means that yeast or epithelial cells may not be as specific with respect to microbial adhesion in screening drugs as would be the actual urothelial receptors.

Although mannose was traditionally regarded as the sole binding site for type 1 fimbriae, several recent studies revealed the complexity of the binding of type 1 fimbriae to its receptors. Sokurenko and coworkers (1992) identified three types of adhesive properties based on the binding of type-1 fimbriated *E. coli* strains to different substrates including mannan, fibronectin, deglycosylated fibronectin and a synthetic peptide corresponding to the N-terminus of fibronectin. Surprisingly, several type 1-fimbriated strains, both clinical and laboratory, bound to deglycosylated fibronectin or even the synthetic peptide, in a mannose-sensitive fashion, suggesting the possible binding to a protein backbone (Sokurenko et al., 1992). In another recent study, Sokurenko et al. (1995) showed that type 1-fimbriated *E. coli* isolates from urinary tract infections had a much higher affinity to immobilized mannan than a group of fecal *E. coli* isolates, suggesting a hitherto unsuspected binding specificity between certain *E. coli* strains and urothelial receptors (Sokurenko et al., 1995). Collectively, these findings strongly suggest that old systems that involve the use of non-urothelial material in studying pathogenesis and drug screening may not be directly relevant for infection by type 1 fimbriated microorganisms. Thus, previous drug screening methods which relied on yeast may not be accurate in detecting which compounds actually inhibit infection, i.e., binding, by type 1-fimbriated microorganisms.

Traditional methods for drug screening have relied upon structure-activity studies and incremental improvement of drug leads by evaluating analogues produced by medicinal chemistry. This is a time-consuming approach that may well overlook many compounds which have completely novel structures.

To facilitate screening large numbers of test samples, which need not be related compounds, a robotic system has recently become available (Heguey et al, 1995). This robotic system enables complete automation of every step in the drug screening process. On-line cell incubation facilities interface with liquid handling systems for diluting and adding test samples, and other units are robotically manipulated in an assay loop that transfers microplates between the plate washed, the reagent addition works station, and a 96-well luminometer. Two robotic arm assemblies are used in each system. Data are captured automatically into a processing network that performs quality control evaluations on each individual microplate assay, as well as rapid data reduction and analysis. Each robotic system can assay up to 10,000 compounds per week. By using multiple targets in the primary screen, efficacy, cytotoxicity, and initial specificity are evaluated rapidly. Compounds of interest identified by the primary screen are then further evaluated in secondary screens and, if necessary, tertiary assays. Animal models are then employed for the final stages of drug development (Heguey et al., 1995).

SUMMARY OF THE INVENTION

It is an object of the present invention to overcome the aforesaid deficiencies in the prior art.

It is another object of the present invention to isolate urothelial type 1 fimbriae receptors.

It is another object of the present invention to treat or inhibit infection by bacteria expressing type 1 fimbriae.

It is a further object of the present invention to screen drugs for treating urinary tract infections.

It is another object of the present invention to treat or inhibit infection by bacteria expressing type 1 fimbriae by administering uromodulin or a derivative thereof.

It is yet another object of the present invention to inhibit binding of bacteria expressing type 1 fimbriae to the urothelial surface.

It has now been discovered that uroplakins Ia and Ib are the major urothelial receptors of type 1 fimbriated microorganisms. By knowing that fimbriated microorganisms bind to these two surface glycoproteins of the urinary tract, it is now possible to screen drugs for treating infections using urothelial type 1 fimbriae receptors. Human, monkey, bovine, murine, and other mammalian urothelial plaques were found to work in the same way, so that screening using bovine or monkey or other mammalian urothelial material is equivalent to screening with the human urothelial plaques. This system is clearly superior to other systems such as the yeast or intestinal cell assays noted above for screening drugs for treating bacterial urinary tract infections, since the urothelial receptors of the present invention are extremely pure, can be isolated in tremendously large quantities (in the range of 20 mg/day), can be stored in the frozen state in small aliquots, and are physiologically relevant for infections by type 1 fimbriated microorganisms. Since the sequence is known for these uroplakins, they can be prepared by genetic engineering rather than isolated from mammalian tissues, where desired.

Since it is now known that bacterial infection occurs by attachment of type 1 fimbriae to uroplakin Ia or uroplakin Ib, this type of infection can now be prevented with compounds that inhibit attachment between the binding site of the bacterial adhesin and the target cell receptor site. Such compounds include the soluble form of the receptor-binding site, antibodies against the receptor-binding site, antibodies against the receptor-binding site of the adhesin, and antireceptor antibodies that occupy the receptor site or soluble adhesins, as well as competitors for uroplakin Ia or Ib.

While type 1 fimbriae can bind in vitro to uroplakins Ia and Ib, ample in vivo data indicate that under normal conditions the access of *E. coli* type 1 fimbriae to their urothelial receptors is extremely limited because of a powerful host defense mechanism. Breakdown of this urinary defense mechanism can lead to an increased susceptibility of the host to *E. coli* infection, possibly leading to recurrent infections.

It has now been found that one candidate soluble receptor is Tamm-Horsfall protein (also named uromodulin), which is the most abundant protein in human urine. Uromodulin represents the major urinary protein that binds to type 1-fimbriated *E. coli*, and this binding is mediated by the high mannose residues present on uromodulin. Moreover, highly purified uromodulin, which is a glycoprotein with high mannose type glycosylation, blocks the in vitro binding of type 1-fimbriated *E. coli* to uroplakins Ia and Ib, thus playing a defensive role against bacterial infection. It is believed that a mannose-rich chain on uromodulin acts as an equivalent to the uroplakin Ia or Ib, and that type 1-fimbriated microorganisms adhere to the mannose-rich chain on uromodulin as well as to uroplakin Ia or Ib.

Accordingly, compounds can be designed to present a mannose moiety to type 1 fimbriated microorganisms to interfere with the adhesion of these microorganisms to uroplakin Ia or Ib. In particular, uromodulin derivatives which include additional mannose moieties can be used to prevent bacterial adhesion to uroplakin Ia or Ib. Alternative competitor compounds can readily be designed, which compounds present mannose moieties to type 1 fimbriated bacteria in the bladder so that the bacteria do not adhere to uroplakin Ia or Ib but rather to the mannose moieties. If the bacteria are not adhered to uroplakin Ia or Ib, the bacteria can readily be flushed out of the bladder in the urine, which can be effected by administering a large volume of liquid to the patient.

Other new types of pharmaceutical agents can be developed which counteract the synthesis of bacterial adhesins responsible for the localization of bacterial pathogens at specific infection (i.e., attachment) sites. It is also believed that by blocking bacterial attachment to host cells, the unattached bacteria are rendered more susceptible to the natural immune defenses of the body and to chemotherapeutic and/or prophylactic drug treatment. A combination of these pharmaceutical agents can be used to inhibit bacterial adhesion. Where an infection is established, these pharmaceutical agents can be used in combination with antibiotics in order to minimize the amount of antibiotic needed to treat the infection. The anti-adhesion pharmaceutical agents present further bacterial colonization of the bladder, and thus reduce the amount of antibiotic required to treat the infection.

Conventional screening methods for antibiotics focus on finding chemicals that are lethal or growth-inhibiting in action against the disease-causing organisms. These screening methods use techniques that detect the efficacy of a chemical's action in affecting growth and viability of test organisms by mechanisms that include interference with cell wall formation, destruction of cellular membranes, and inhibition of biosynthesis or nutrient uptake. Therefore, conventional screening methods dependent upon inhibition of growth and viability are in that respect limited to the kinds of antibiotic producers that can be identified.

The present invention thus provides a convenient, powerful and physiologically relevant method for screening new drugs that can interfere with the binding of type 1 fimbriated *E. coli* or similar microorganisms to urothelial receptors. Drugs found to be effective in interfering with this binding can be delivered orally or parenterally, as well as by any other conventional means, and can be accumulated in vivo to provide an effective concentration in the urine, making this method extremely effective in preventing and treating bacterial infections.

Since it has now been discovered that adhesion of type 1 fimbriated microorganisms to the uroplakins can indeed be inhibited by compounds that interfere with this adhesion, effective drugs for preventing such bacterial infection can be based on compounds that inhibit such adhesion. Testing interference of adhesion of microorganisms to uroplakins can be conducted on a great number of compounds at one time using a high throughput robotic assay. It is thus possible to screen large numbers of compounds using robots, simply by observing the adhesion or non-adhesion of the microorganisms in question to the uroplakins in the presence of individual compounds or combinations of compounds. Mannose can be used as a positive control in these assays, as mannose is known to inhibit adhesion of these microorganisms to the uroplakins.

BRIEF DESCRIPTION OF THE DRAWINGS

FIG. 6A is the partial amino acid sequence of bovine uroplakin Ia (primary data) (SEQ ID NOs:1–5); FIG. 6B is cDNA-deduced sequences (SEQ ID NOs:6–11).

FIG. 7 shows the deoxynucleotide and cDNA-deduced amino acid sequence of bovine uroplakin Ia (SEQ ID NOs:12 and 13).

FIG. 8 shows the deoxynucleotide and cDNA-deduced amino acid sequence of bovine uroplakin Ib (SEQ ID NOs:14 and 15).

DETAILED DESCRIPTION OF THE INVENTION

Figure 1B:
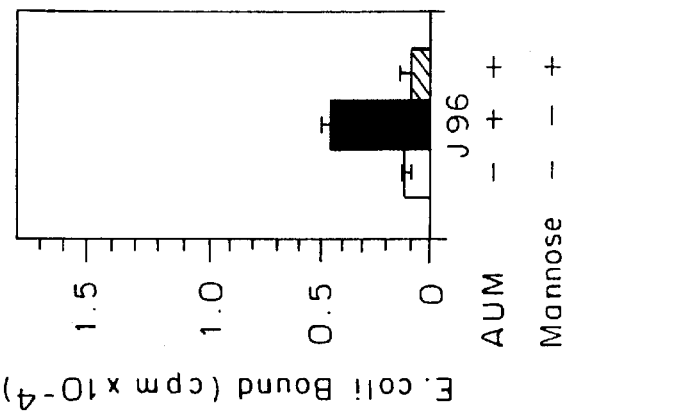
FIGS. 1A and 1B are graphs showing in vitro adherence of type 1-fimbriated *E. coli* to bovine urothelial plaques.

Now that it has been determined that microorganisms with type 1 fimbriae bind to urothelial receptors such as uroplakin Ia and uroplakin Ib, potential drugs for treating urinary tract infections can be screened quickly and inexpensively by testing if the compound of interest inhibits microbial binding to isolated urothelial receptors. Since the synthesis of bacterial adhesins is influenced by, for example, antibiotics, antibacterial agents thus may be used not only for their antibacterial effect but also for their ability to interfere with bacterial attachment. Attachment between the binding site of the bacterial adhesin and the target cell receptor can be inhibited by the soluble form of the receptor-binding site, antibodies against the receptor-binding site, antibodies against the receptor-binding site of the adhesin, and antireceptor antibodies that occupy the receptor site or soluble adhesins. Compounds that alter the glycosylation of the host cells can also change the receptor phenotype.

Because it has now been determined that microbial infection of type 1-fimbriated microorganisms may be inhibited or prevented by interfering with microbial adhesion to uroplakins rather than by specific toxicity of compounds to bacteria, it is possible to provide treatment for infections which is not dependent upon antibiotics, so that there is less chance that the bacteria develop a resistance to the compound. Alternatively, the adhesion-inhibiting compounds can be administered in conjunction with antibiotics, resulting in the use of lower dosages of antibiotics to rid the patient of infection by bacteria bearing type 1 fimbriae.

According to the present invention, compounds can be tested for their efficacy in inhibiting adherence of microorganisms to mannose-containing receptors such as uroplakins, and thus for their efficacy in inhibiting or preventing infection by these microorganisms in tissues which contain these receptors, such as uroepithelial tissue. To test such compounds, purified urothelial plaques, which may contain uroplakin Ia, uroplakin Ib, mixtures of uroplakin Ia and uroplakin Ib, or mixtures of at least one of uroplakin Ia and uroplakin Ib with at least one of uroplakin II and uroplakin III, are admixed in a suitable buffer with the compound to be tested. Labeled microorganisms which bind to the urothelial receptors, i.e., type 1 fimbriated microorganisms, are introduced into the mixture of subject compound and purified urothelial plaques and the mixture is incubated at appropriate temperatures for a sufficient time to allow adhesion of the microorganisms to the urothelial plaques. After this period of time, which may differ depending upon the microorganism being tested, and which can be readily discerned by one skilled in the art, the mixture is treated to remove unadhered microorganisms and the microorganism-receptors remaining are assayed for the amount of microorganism adhered to the receptors.

An alternative technique is to absorb the urothelial plaques on nitrocellulose paper or other paper prior to performing the bacterial binders assays.

For these assays, the microorganisms can be labeled by any conventional label which can be used to quantify and/or identify the microorganisms. Such conventional labels include, but are not limited to, radioisotopes, biotin-avidin labels, chromophoric labels, enzymes and the like, all of which are well known to those skilled in the art.

The microorganisms can be labeled with radionuclides, and then the labeled microorganisms can be detected using radio counters. Alternatively, the microorganisms can be labeled with a fluorescent compound. When the fluorescently labeled microorganism is exposed to light of the proper wavelength, its presence can then be detected due to fluorescence. Among the most commonly used fluorescent labelling compounds are fluorescein isothiocyanate, rhodamine, phycoerythrin, phycocyanin, allophycocyanin, o-phthaldehyde, and fluorescamine.

The microorganisms can also be detectably labeled using fluorescence emitting metals. These metals can be attached to the microorganisms using such metal chelating groups as diethylenetriamine pentaacetic acid (ETPA).

The microorganisms can also be detectably labeled by coupling to biotin. Biotinylated microorganisms can then be detected by avidin or streptavidin coupled to a fluorescent compound or to an enzyme such as peroxidase to a radioactive isotope and the like.

For the purpose of the present invention, the purified urothelial plaques can contain any desired combination of uroplakins. Since it has been demonstrated that uroplakins Ia and Ib can be cross-linked to uroplakins II and III, respectively, combinations of these uroplakins can be used to screen compounds for efficacy in treating or preventing infections by microorganisms which adhere by type 1 frimbrial adhesion.

Potential adhesion-preventing or inhibiting compounds can be screened robotically. For example, a system can be used which identifies, under computer control, compounds from a compound database which exhibit improved activity in inhibiting adhesion of microorganisms bearing type 1 fimbriae to uroplakins Ia and/or Ib.

An analysis robot analyzes the compounds in the compound database by any known method to analyze for inhibition of binding of microorganisms bearing type 1 fimbriae to uroplakins Ia and/or Ib. The analysis robot further analyzes the compounds to obtain other pertinent data, such as data pertaining to the compounds' composition, composition, structure and electronic structure.

Preferably, elements of the apparatus used for analysis are controlled by a data processing device, such as a computer operating in accordance with software. Consequently, it is possible in the present invention to store massive amounts of data and to utilize this data in a current iteration to generate instructions to the robot as to which types of compounds would be likely candidates for binding inhibition. It is also possible to use the historical structure-activity data obtained during previous iterations (or any subset of previous iterations, as determined by user input). Thus, at subsequent iterations of the analysis of compounds, the compounds identified may be better at inhibiting adhesion than compounds tested in previous iterations.

As a specific example, derivatives of uromodulin which have a variety of mannose chain substitutions, additions, etc. can be tested by the robot for inhibition of adhesion by microorganisms bearing type 1 fimbriae to uroplakins Ia and/or Ib. Once the optimum compounds are identified, the compounds are analyzed by an analysis robot for, e.g., the type(s) of groups on the compounds that inhibit the binding sought to be inhibited. This structure-activity data is then used for identifying or synthesizing additional compounds that are potential inhibitors of binding of type 1 fimbriae to uroplakins Ia and/or Ib.

For treating or preventing infection by microorganisms bearing type 1 fimbriae, soluble derivatives or analogues of uroplakin Ia or uroplakin Ib can be administered. The soluble derivative or analogue of uroplakin Ia or uroplakin Ib interferes with bacterial attachment via type 1 fimbriae to the uroplakin Ia or uroplakin Ib in a patient, thus preventing infection and leaving the bacteria in a position where they are more likely to be adversely affected by antibacterial compounds or the body's own defenses against such microorganisms.

In another embodiment of the present invention, effective amounts of uromodulin or a derivative thereof which has been found to inhibit binding of type 1-fimbriated microorganisms are administered to block binding of type 1-fimbriated *E. coli* to uroplakins Ia and Ib. It is believed that uromodulin blocks adhesion of type 1-fimbriated microorganisms because of its high mannose glycosylation. For example, uromodulin from pregnant women bears a longer (Man-7) high mannose chain than does regular uromodulin. This difference can account for the reason uromodulin from pregnant women is ten times more potent as an immunosuppressant than is regular uromodulin. In diabetic patients, the binding of furosemide, a diuretic, to uromodulin is much higher than to uromodulin in normal patients. This has been attributed to altered uromodulin glycosylation or to lack of sufficient uromodulin present in the bladder to prevent adhesion of type 1 fimbriae bearing microorganisms. Therefore, by altering the amount and kind of mannose glycosylation, of uromodulin, additional compounds can be made to inhibit and treat urinary tract infections.

In addition to uromodulin and its derivatives with mannose chains, other compounds which have mannose chains which compete with uroplakins Ia and Ib can be administered to interfere with adherence of microorganisms bearing type 1 fimbriae to the urothelial surface. These compounds having mannose chains compete with the uroplakins Ia and Ib for the type 1 fimbriae. As the microorganisms bearing type 1 fimbriae encounter the mannose-chain compounds, the microorganisms bind to these compounds rather than to uroplakins Ia and Ib. Thus, administering to a patient an effective amount of a competitor to uroplakins Ia and Ib can prevent the microorganisms from colonizing the bladder, as the microorganisms attached to the mannose-chain compounds are readily flushed from the bladder with urine.

Many women who are susceptible to urinary tract infections are likely to be infected following sexual intercourse. A compound bearing mannose chains that competes with uroplakins Ia and Ib for bacterial binding can be administered to such women after intercourse to prevent a urinary tract infection.

Alternatively, an antibody against the receptor-binding site can be administered to treat or prevent infection by bacteria expressing type 1 fimbriae. Such an antibody can be prepared by conventional techniques, and competes with the bacteria for attachment to the uroplakin Ia or uroplakin Ib sites.

Antibodies against the receptor-binding site of the adhesion can also be used to treat or prevent infection by type 1 fimbriae-expressing bacteria. These antibodies can be prepared from adhesion antigens and administered by one skilled in the art without undue experimentation.

Antireceptor antibodies that occupy the receptor site or soluble adhesins can also be administered to treat or prevent infection by bacteria expressing type 1 fimbriae. These antireceptor antibodies also compete with bacteria expressing type 1 fimbriae for binding sites on the uroplakin Ia and uroplakin Ib receptors.

Uroplakins

Several major protein components of bovine asymmetrical unit membrane have recently been identified, (Wu et al., 1992). Using an improved procedure, Wu et al., (1994) isolated asymmetric unit membranes from nine mammalian species, including cattle, human, monkey, sheep, pig, dog, rabbit, rat and mouse. The asymmetrical unit membranes of these species appear morphologically similar, bearing crystalline patches of 12-nm protein particles with a center-to-center pacing of 16.5 nm (Waltz et al., 1995).

Recent molecular cloning data indicated that both uroplakins II and III possess a single membrane spanning domain (Lin et al., 1994; Wu and Sun, 1993). Further biochemical and molecular cloning studies on the 27-kDa uroplakin I has revealed the existence of two related proteins encoded by separate genes (Yu et al., 1994). These two proteins, now known as uroplakin Ia and uroplakin Ib, show 39% sequence identity, and they are structurally similar in that both possess four transmembrane domains with two hydrophilic loops extending into the bladder lumen.

Antibodies raised against synthetic oligopeptides or individual bovine uroplakins were used to establish by immunoblotting that the four uroplakins are present in asymmetrical unit membranes of all nine species (Wu et al., 1994). The DNA-deduced amino acid sequences of bovine and mouse uroplakin II revealed 83% identity (Wu et al., 1994). Uroplakins Ia, Ib, II and III are the major protein components of probably all mammalian urothelial plaques, and the sequence and three dimensional structure of uroplakin molecules have been highly conserved during mammalian evolution (Wu et al., 1994).

Wu et al., (1994) showed that uroplakin Ia is highly conserved with respect to its apparent size and some of its antigenic determinants. Although uroplakin Ib showed some variations in its size and in two of its epitopes, the use of an affinity-purified polyclonal antibody clearly identified the uroplakin Ib homologues in all mammalian species tested.

Although uroplakin Ia and uroplakin Ib are encoded by separate genes located on different chromosomes (Ryan et al, 1990), they are structurally conserved in that both have four potential transmembrane domains with only two major hydrophilic loops, i.e., those interconnecting transmembrane domain ½ and ¾, extending into the lumian space (Yu et al., 1994). Computer searches of the entire GenBank revealed that the uroplakin Ib sequence is almost identical to a hypothetical protein encoded by a transforming growth factor β-inducible (TI-1) gene of a mink lung epithelial cell line (ref.). Moreover, the uroplakin Ia and Ib sequences, as a group, are homologous to a novel family of cell surface proteins including CD9, CD37, CD53, and CD63, many of which are important leukocyte cell surface differentiation or tumor-associated antigens (Yu et al., 1994). Another important property shared by all members of this gene family is that they all have several highly conserved cysteine residues located in the major luminal loop connecting the third and fourth transmembrane domains (Yu et al., 1994). Some of these cysteines are involved in forming intramolecular disulfide bonds possibly capable of stabilizing the conformation of this major luminal loop. The two uroplakin I molecules differ in that uroplakin Ia is more conserved and can exist as a homodimer (Wu et al., 1994). Co-purification data indicate that uroplakin Ib, and possibly uroplakin Ia, can bind to uroplakin II and uroplakin III.

Wu et al., (1994), found that asymmetric unit membranes from cattle, humans, monkeys, sheep, pigs, dogs, rabbits, rat, and mouse appear morphologically similar, bearing crystalline patches of 12-nm protein particles with a center-to-center packing 16.5 nm. Using antibodies raised against synthetic oligopeptides or individual bovine uroplakins, it was established by immunoblotting that the four uroplakins are present in asymmetric unit membranes of all of these species. The DNA-deduced amino acid sequences of bovine and mouse uroplakin II revealed 83% identity, indicating that uroplakins Ia, Ib, II and III are the major protein components of probably all mammalian urothelial plaques, and that the sequence and three-dimensional structure of uroplakin molecules are highly conserved during mammalian evolution.

Molecular cloning of bovine uroplakin cDNAs has been described by Yu et al., 1994 for uroplakin Ia and uroplakin Ib; by Lin et al., 1994, for uroplakin II; and by Wu and Sun, 1993 for uroplakin III. For cloning of the mouse uroplakin II gene, a 730-base pair uroplakin II cDNA was labeled with [$^{32}$P]dCTP and used as a probe to screen a mouse genomic library constructed in a lambdaEMBL3-SP6/T7 vector (Clontech). Approximately 4×10$^6$ recombinant phage were plated, lifted onto nitrocellulose filters, and hybridized with The antigenic specificity of rabbit uroplakin antibodies were shown by immunoblotting to be monospecific for the corresponding uroplakin subunits. The amino acid sequences of uroplakins Ia and Ib, uroplakin II and uroplakin III are according to Yu et al., 1994, are shown in Table 1, Lin et al., 1994 and Wu and Sun, 1993, respectively.

TABLE 1

Antigenic Specificity of the Uroplakin Antibodies
All of these are rabbit antibodies, which by immunoblotting were shown to be monospecific for the corresponding uroplakin subunits. The amino acid sequences of UPIa and Ib, II, and III are according to Yu et al. (1994); Lin et al. (1994); and Wu and Sun(1993), respectively.

| Uroplakin | $M_r$ | Antibody Designation | Epitope | Corresponds to Amino Acid r |
|---|---|---|---|---|
| Ia | 27 | UPIa-2UPa-4 | VIADQYRIYPLMGVSGKDDDNSQGRELTRLWDR | 41–59 of SEQ ID NO:13 |
|  |  |  |  | 139–152 of SEQ ID NO:13 |
| Ib | 28 | UPIb-1 | AKDDSTVRCFQGLLIFGN | 2–19 of SEQ ID NO:15 |
|  |  | UPIb-2UPIb-AUM | QNNSPPNNDDQWKNNGVTKT Polyclonal | 130–149 of SEQ ID NO:15? |
| II | 15 | UPII-N | ELVSVVDSGSG | 1–11 of UPII (SEQ ID NO:17) |
|  |  | UPII-C | DSGSGFTVTRLSA | 7–19 of UPII (SEQ ID NO:18) |
|  |  | UPII-2UPII-3 | SAYQVTNLAPGTKYYIGASTESSREIPMSTFPRRK | 18–33 of UPII (SEQ ID NO:19) |
|  |  |  |  | 40–58 of UPII (SEQ ID NO:20) |
| III | 47 | UPIII | Polyclonal | ? | a $^{32}$P-labeled cDNA probe at 60° C. for sixteen hours in 6×SSPE (1 M NaCl, 60 mM NaH$_2$PO$_4$, 5 mM EDTA), 5×Denhardt's solution (0.1% polyvinylpyrrolidone, 0.1% bovine serum albumin, 0.1% Ficoll), 0.1% SDS, and 100 microg/ml denatured salmon sperm DNA. These filters were washed in 2×SSC, 0.1% SDS at room temperature twice each for 30 minutes, in 1×SSC, 0.1% SDS at room temperature twice each for 30 minutes, in 1×SSC, 0.1% SDS at 60° C. twice each for 20 minutes, and then autoradiographed at −70° C. overnight. Two clones containing overlapping genomic DNA inserts that spanned about 25-kilobase pairs were purified and digested with restriction endonucleases. The resulting fragments were subcloned into pGEM7Z and sequenced by the dideoxynucleotide chain termination method of Sanger et al. using a T7DNA Sequenase Kit (U.S. Biochemical Corp.). The genomic DNA sequences were analyzed using a GCG7 computer package.

With respect to specific structural properties of asymmetric unit membranes, electron microscopic examination of asymmetric unit membranes of cattle, human, monkeys, sheep, pigs, dogs, rabbit, rat and mouse revealed that the asymmetric unit membranes of these diverse mammals contained 12-nm protein particles which formed hexagonally packed crystalline packages. Digital image averaging in all species showed a six-fold symmetric unit cell (i.e., the 12-nm particles) which consists of six stain-excluding regions surrounding a stain-filled central depression. Each of these six elongated stain-excluding regions has a distinct, right-handed kink and can be resolved into an inner and an outer globular domain. The six inner domains with an average diameter of 3.3 nm define an inner annulus, centered at a radius of 3.7 nm, and the six outer domains with an average diameter of 2.7 nm define an outer annulus, centered at a radius of 6.6 nm. The six inner domains are rotated by about 12° counterclockwise, and the six outer domains by about 20° clockwise relative to the hexagonal lattice lines. In addition, there are two types of stain-excluding bridges, one connecting adjacent inner domains with each other, and the other connecting each inner domain with its closest outer domain.

SDS-PAGE immunoblotting and cDNA/gene sequence data have clearly established that uroplakin II is highly conserved during mammalian evolution, suggesting that it is functionally important. According to its cDNA-deduced protein sequence, and some actual protein data, it has been shown that bovine uroplakin II is synthesized as a 28-kDa precursor with an NH$_2$-terminal signal peptide followed by a heavily glycosylated presequence, which may be important in regulating the ability of uroplakin II to interact with other uroplakins to form the highly insoluble uroplakin complex. Mature bovine uroplakin II consists of 100 largely hydrophilic amino acids which are predicted to form multiple beta sheets. The protein is anchored in the membrane through a COOH-terminal tail of hydrophobic, potential transmembrane domain. Consistent with the fact that the electrophoretic mobility of the protein is not affected by deglycosylation, mature bovine uroplakin II does not contain a potential N-glycosylation site based on its cDNA-deduced primary sequence. Mouse genomic DNA-derived data showed, however, that mouse uroplakin II contains a potential N-glycosylation site.

Uroplakin III, like other uroplakins, is expressed in the umbrella cells of the urothelium, indicating that its expression is tissue-specific and differentiation-dependent (Wu, 1993). Bovine uroplakin III contains approximately 20 kDa equivalents of complex-type sugars, and its core protein consist of 269 amino acids. A unique feature of uroplakin III is that it is the only uroplakin known to possess a significant cytoplasmic domain (Wu, 1993).

Preparation of Asymmetric Unit Membranes from Mammalian Urinary Bladders

Asymmetric unit membranes were isolated from urinary bladders of cattle, human, monkey and mouse by sucrose gradient centrifugation followed by Sarkosyl and NaOH wash (Wu et al., 1992; 1994). The asymmetric unit membranes dissolved in 1% SDS were quantitated using bicinchoninic acid reagent (Pierce).

Determining Fimbrial Specificity by Agglutination Tests

Yeast and erythrocyte agglutination tests were performed on glass slides. Briefly, 5 microliters of radiolabelled bacteria (10$^{10}$ cells per ml) were mixed with 10 microliters of 1% (wt/vol) Saccharomyces cerevisiae suspended in PBS.

Human P1 erythrocytes were identified by their agglutinability with anti-P1 antisera (Immucor, Morcross, Calif.). For hemagglutination, citrated whole blood was washed three times with PBS by centrifugation at 500×g. Ten microliters of washed erythrocytes (4%) were mixed with an equal volume of radiolabelled bacteria ($10^{10}$ cells per ml). After the mixtures were incubated at room temperature for five minutes, the agglutination was read, both macroscopically and microscopically, and graded (−, + to ++++). In some of the experiments, the bacterial suspension was 2% in D-mannose before its incubation with yeast or erythrocytes.

E. coli Strains Expressing Defined Fimbrial Adhesins

The fimbrial adhesins of various E. coli strains were assessed by their abilities to agglutinate yeast, as well as erythrocytes of various animal species, in the absence and presence of D-mannose, as shown in Table 2. J96 is a human pyelonephritis isolate that agglutinated yeast and guinea pig erythrocytes in a mannose-sensitive fashion; this agglutination property suggests that it expresses type 1 fimbriae that harbor FimH adhesins. In addition, it agglutinated erythrocytes of human, sheep and rabbit in a mannose-resistant fashion. This is consistent with the fact that J96 also expresses P fimbriae carrying G-1 and G-3 adhesins. SH48 and HU849 are recombinant derivatives of nonfimbriated P678-54 (an E. coli K-12 derivative) through transfections using J96 genomic DNAs encoding type 1 or P fimbriae, respectively. These two strains collectively exhibit the chemical, serological, and functional properties of their parent strain, J96. SH48 strongly agglutinated, in a mannose-sensitive manner, yeast and erythrocytes of all species tested; this result confirmed that SH48 expresses exclusively type 1 fimbriae. HU849 strongly agglutinated human and rabbit erythrocytes (mannose-resistant), confirming its production of G-1 adhesin. The recombinant strain IA2 (HB101/pCD1) agglutinated human and sheep erythrocytes, consistent with its expression of P fimbriae carrying G-2 adhesin. As expected, the nonfimbriated E. coli P678-54 were nonagglutinating. These results, summarized in Table 2, established that all E. coli strains expressed, under current culture conditions, the expected fimbrial adhesins.

pended in PBS containing 30% glycerol, and stored at about −70° C. until use.

In Vitro Bacterial Adherence Assay

Purified asymmetric unit membranes were suspended in PBS and incubated in 96-well polystyrene microtiter plates at room temperature for 30 minutes, then at 4° C. for 16 hours. All subsequent steps were carried out at room temperature. After being washed three times with PBS for two hours, the immobilized asymmetric membrane units were incubated with 2% BSA in PBS for two hours, and $^{35}$S-labelled bacteria were incubated in 2% BSA and 0.1% $NaN_3$ for two hours. The wells were then washed four times with PBS, and the bound bacteria were dissolved in 1% SDS for 30 minutes and quantitated by scintillation counting. All binding studies were performed in triplicate.

Bacterial Overlay Assay

Asymmetric unit membrane proteins were resolved by SDS/PAGE (17% acrylamide; acrylamide/bisacrylamide= 10:1) and electrophoretically transferred to nitrocellulose. After a brief incubation in 3% BSA in PBS to block the unoccupied sites, the nitrocellulose sheet was incubated with $^{35}$[S]methionine-labelled bacteria in 2% BSA and 0.1% $NaN_3$. After three washings in PBS, the nitrocellulose was air-dried and autoradiographed.

Enzymatic Deglycosylation

Purified asymmetric unit membranes were dissolved in 0.1% SDS at room temperature. The solution was adjusted to a final concentration of 1% octyl glucoside, 0.05% $NaN_3$, 5 mM EDTA, 50 mM sodium acetate buffer (pH 5.5), and 33 milliunits/ml endoglycosidase(endo)H. Another fraction was made to contain 40 mM sodium phosphate buffer (pH 7.4) and 14 units/ml N-glycosidase F (Boehringer Mannheim). After the mixtures were incubated at 37° C. for 16 hours, the proteins were resolved by SDS/PAGE and either stained by silver nitrate or blotted onto nitrocellulose for the bacterial overlay assay.

Type 1-Fimbriated E. coli Bind to Isolated Urothelial Plaques

To determine whether the asymmetric unit membrane proteins can serve as E. coli receptors, the binding of five strains of $^{35}$[S]methionine-labelled, type 1- and P-fimbriated

TABLE 2

E. coli Strains and Their Adhesive Properties*

| Strain | Hemagglutination (species) Yeast† Agglutination | Guinea Pig | Human‡ | Sheep | Rabbit | Horse | Adhesin 1 | P | AUM Binding |
|---|---|---|---|---|---|---|---|---|---|
| J96 | ++/−§ | ++/− | +/+ | +/+ | ++/+ | ++/− | H¶ | G-1, G-3→ | ++/− |
| SH48 | ++++/− | ++++/− | +++/− | ++/− | +++/− | +++/− | II | — | +++/− |
| HU849 | −/− | −/− | +++/+++ | −/− | +++/+++ | −/− | — | G-1 | −/− |
| IA$_2$ | −/− | −/− | +++/+++ | ++/++ | −/− | −/− | — | G-2 | −/− |
| P678-54 | −/− | −/− | −/− | −/− | −/− | −/− | — | — | −/− |

*The degree of agglutination and AUM binding was graded from ++++ to − to denote strong negative reactions.
†S. cerevisiae.
‡Human P1 erythrocytes.
§Values before and after the slash denote the degrees of agglutination in the absence and presence of 2% D-mannose, respectively.
¶FimH adhesin of type 1 fimbriae. → G-1, G-2, and G-3 are the three major types of adhesins of P fimbriae.

The bacteria were grown in Luria-Bertani medium for 16 hours and labelled with $^{34}$[S]methionine [DuPont/NEN] specific activity>1000 Ci/mmol (1 Ci-37 Gbq) in a methionine- and glucose-free medium at 37° C. for two hours. The labelled bacteria were washed three times, resus- E. coli to highly purified bovine asymmetric unit membranes was tested using an in vitro adherence assay. Bovine urothelial plaques were isolated by discontinuous sucrose gradient centrifugation plus detergent wash, taking advantage of the remarkable insolubility of asymmetric unit membranes in many detergents, including 2% Sarkosyl (Wu, 1992; 1994). After negative staining, these highly purified plaques exhibit two-dimensional crystalline arrays of 16-nm protein particles and give rise to four major uroplakin bands by SDS/PAGE. In the binding assay, purified asymmetric unit membranes were used to coat the wells of a microtiter plate and incubated with $^{35}$S-labelled E. coli, and the radioactivities of the bound bacteria, dissolved in 1% SDS, were quantitated. Of the bacterial strains expressing both type 1 and P (strain J96), type I only (SH48), P only (HU849 and IA2), or neither (P678-54 as a control), only the first two type 1-fimbriated E. coli were able to bind the asymmetric unit membranes, as shown in FIG. 1A. Although J96 expresses both type 1 and P fimbriae (of the G-1 and G-3 types), its binding to asymmetrical unit membranes could be completely blocked by mannose, suggesting that the type 1, but not the P, fimbrial adhesin was responsible for the observed binding, as can be seen from FIG. 1B.

FIG. 1A shows the in vitro binding of various E. coli strains to bovine urothelial plaques. Purified bovine urothelial plaques, consisting of asymmetric unit membranes that cover 70–80% of the urothelial apical surface, were immobilized on microtiter wells (0.2 microgram per well). The unoccupied binding sites were blocked with 3% BSA in PBS. BSA was used to coat the control wells. The E. coli strains used were J96, which express type 1 fimbriae as well as P fimbriae carrying the G-1 and G-2 adhesins; SH48, which expresses type 1 fimbriae only; HU849, which expresses P fimbriae carrying G-1 adhesin; IA2, which expresses P fimbriae carrying G-adhesins; and nonfimbriated P678-54.

$^{35}$[S]methionine-labelled bacteria were added to each well ($2\times10^5$ cpm in $10^7$ bacteria suspended in PBS). After incubation at 25° C. for two hours, the wells were washed with PBS and the radioactivities of the bound bacteria, dissolved in 1% SDS, were counted. Each value represents the means of triplicates bracketed by the standard deviation (±15%). It should be noted that only the type 1-fimbriated J96 and SH48 strains, but not the P-expressing HU849 and IA2 or the nonfimbriated P678-54, adhered to the asymmetric unit membranes.

Figure 1A:
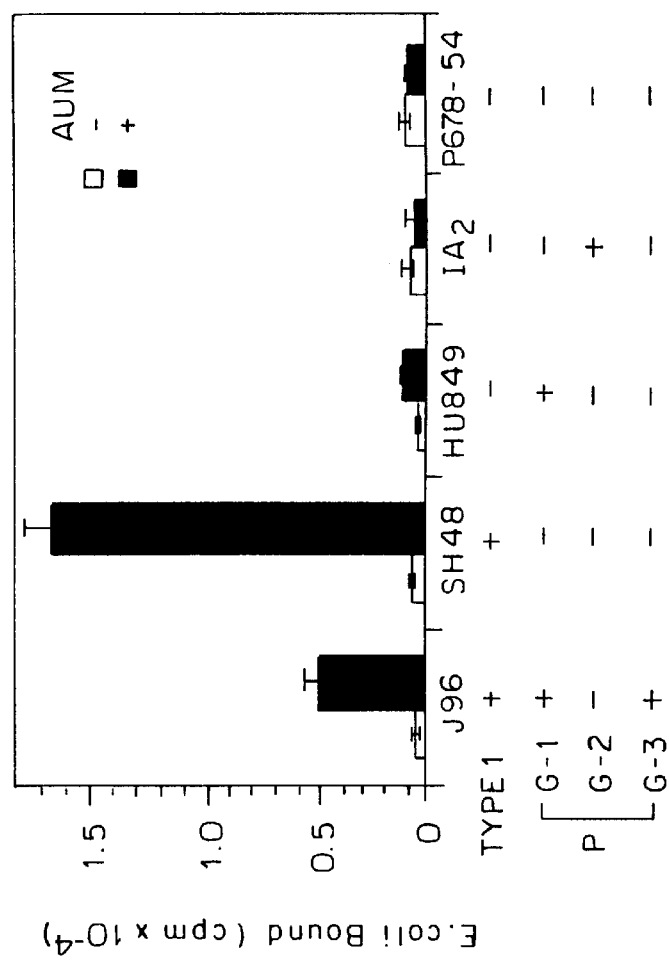

In FIG. 1B, the relative contribution of type 1 and P fimbriae in the binding of J96 to asymmetric unit membranes is shown. $^{35}$S-labelled J96 ($2\times10^5$ cpm) were incubated with immobilized asymmetric unit membranes in the absence or the presence of 2% D-mannose. It should be noted that the binding of J96 to asymmetric unit membranes could be completely blocked by mannose.

Figure 2:
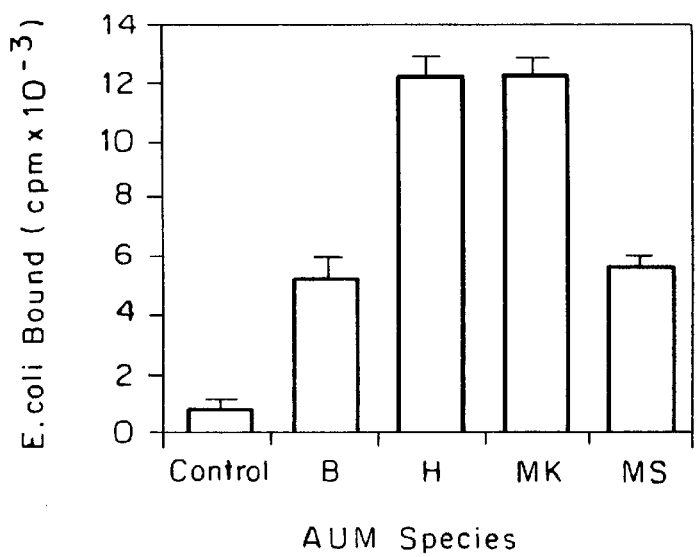
FIG. 2 is a graph showing in vitro binding of type 1-fimbriated bacteria to asymmetric unit membranes of various mammalian species.
Figure 3A:
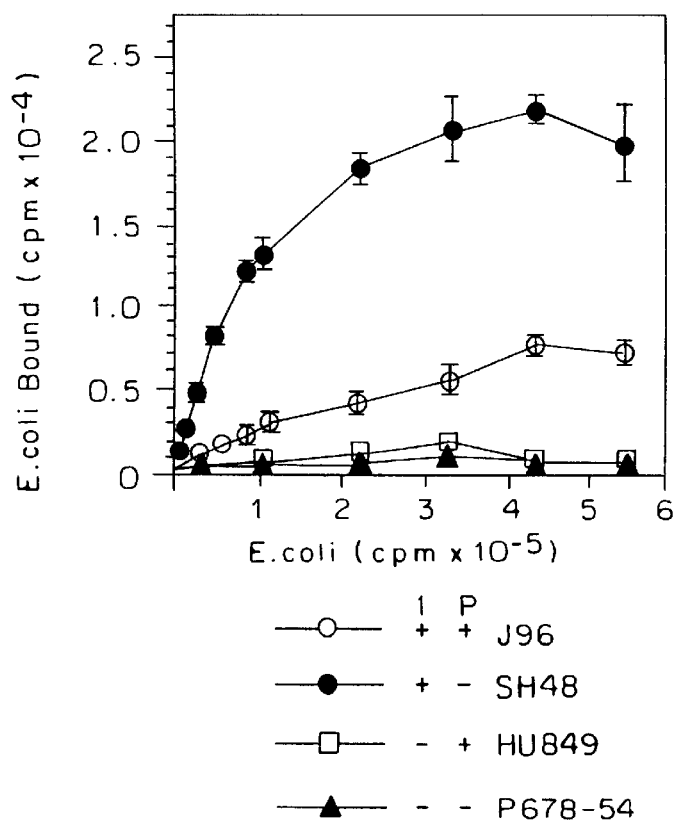
FIGS. 3A and 3B are graphs showing the saturation kinetics of bacterial binding to bovine urothelial plaques.
Figure 3B:
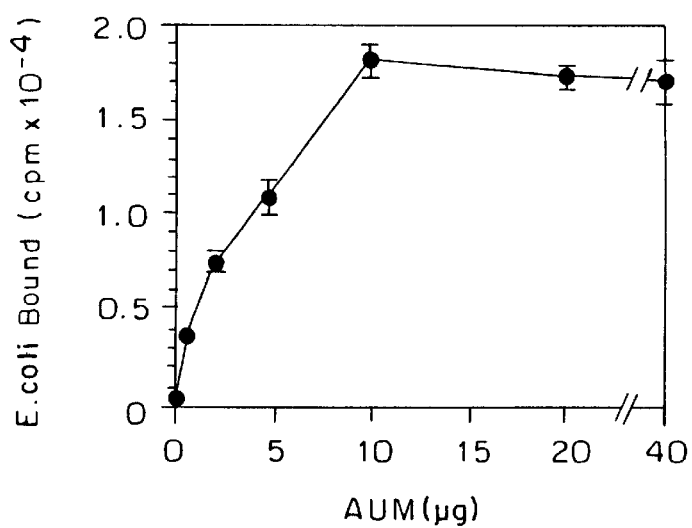

To test whether the binding between type 1 fimbriae and asymmetrical unit membranes was species-specific, an in vitro adherence assay was performed using asymmetric unit membranes isolated from bovine, human, monkey and mouse bladders (FIG. 2). The fact that asymmetric unit membranes of all these species showed strong binding suggests that the urothelial plaque receptors are highly conserved. Moreover, with a constant amount of immobilized asymmetric unit membrane, this binding was linearly proportional to the bacterial input and was saturable (FIG. 3A). Reversing the experiment by immobilizing increasing amounts of asymmetric membrane units with a constant bacterial input yielded similar saturating kinetics (FIG. 3B). These data clearly indicate that type 1-fimbriated, but not the P-fimbriated, E. coli can bind specifically to the asymmetric unit membrane plaques that cover the bulk of the urothelial apical surface.

Specifically, FIG. 2 illustrates in vitro binding of type 1-fimbriated bacteria to asymmetric unit membranes of various mammalian species. The asymmetric unit membranes of cattle (B), human (H), monkey (MK) and mouse (MS) were immobilized on microtiter wells and incubated with radiolabelled, type 1-fimbriated E. coli (strain SH48). The bacteria bound to the asymmetric unit membranes of all four species.

To test the effects of sugars on the binding of type-1 fimbriated E. coli to bovine urothelial plaques, $2\times10^5$ cpm of radiolabeled E. coli (SH48) were preincubated with D-mannose (Man), methyl-α-D-mannopyranoside(MMP), or D-galactose (Gal) before they were incubated with 0.2 μg of immobilized bovine asymmetrical unit membranes. The bacterial binding to the asymmetrical unit membranes was greatly inhibited by D-mannose and its analog methyl-α-D-mannopyranoside, but not by D-galactose.

UPIa and UPIb as Receptors of Type 1-Fimbriated E. coli

Figure 4:
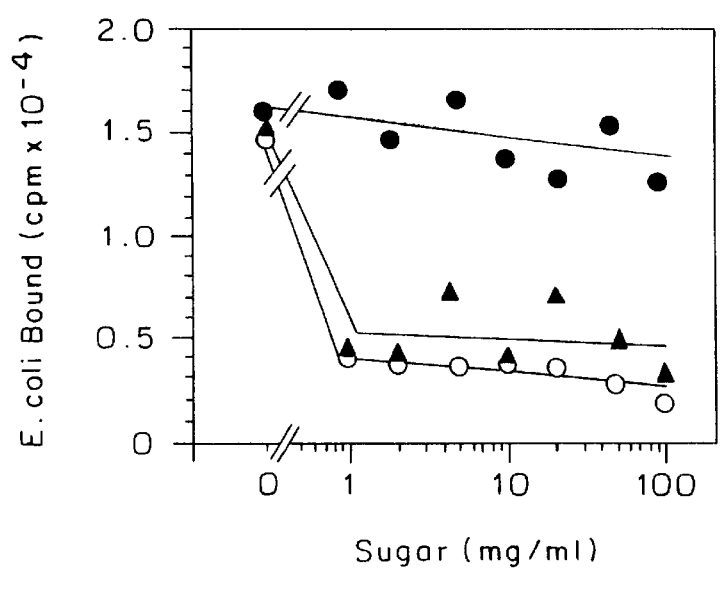
FIG. 4 is a graph showing the effects of sugars on the binding of type 1-fimbriated *E. coli* to bovine urothelial plaques. Radio labelled *E. coli* to bovine urothelial plaques.

To determine which of the asymmetric membrane proteins are responsible for this binding, a gel overlay assay was performed. Uroplakins were resolved by SDS/PAGE (cf. FIGS. 5A and 5B), transferred to nitrocellulose, and incubated with radiolabelled bacteria. Autoradiography showed that, similar to the results obtained with intact asymmetric unit membranes, only type 1-fimbriated bacteria bound protein bands, as shown in FIG. 5C, and the binding could be inhibited by mannose but not by galactose. The two major bacterial binding proteins were identified as the two closely related uroplakin proteins, i.e., the 27 kDa-uroplakin Ia and the 28 kDa-uroplakin Ib, according to their sizes and immunoreactivities (FIG. 5B, lanes 1 and 2). No binding was observed with the mature uroplakin II, which is not glycosylated, or with uroplakin III which is glycosylated with 20 kDa equivalents of complex type sugars (FIG. 5C and D). To determine whether the carbohydrate moieties of uroplakin I proteins were responsible for the binding of the type 1 fimbriae, as one might expect from the inhibitory effects of mannose (cf. FIG. 4), the effects of deglycosylation were tested, results shown in FIGS. 5D and E. Endo H removed about 3-uroplakin I equivalents of sugars from uroplakin I proteins (cf. FIG. 5D, lanes 2 and 5). This abolished the ability of uroplakin I molecules to bind the bacteria (FIG. 5E, lanes 2 and 5). These results provide additional evidence for the specificity of the in vitro type 1 fimbriae-asymmetric unit membrane interaction. Moreover, the data established that uroplakin Ia and uroplakin Ib are the main asymmetric unit membrane-associated receptors for type 1-fimbriated bacteria and that the high-mannose type sugars of the uroplakin I proteins are responsible for the binding.

Figure 5:
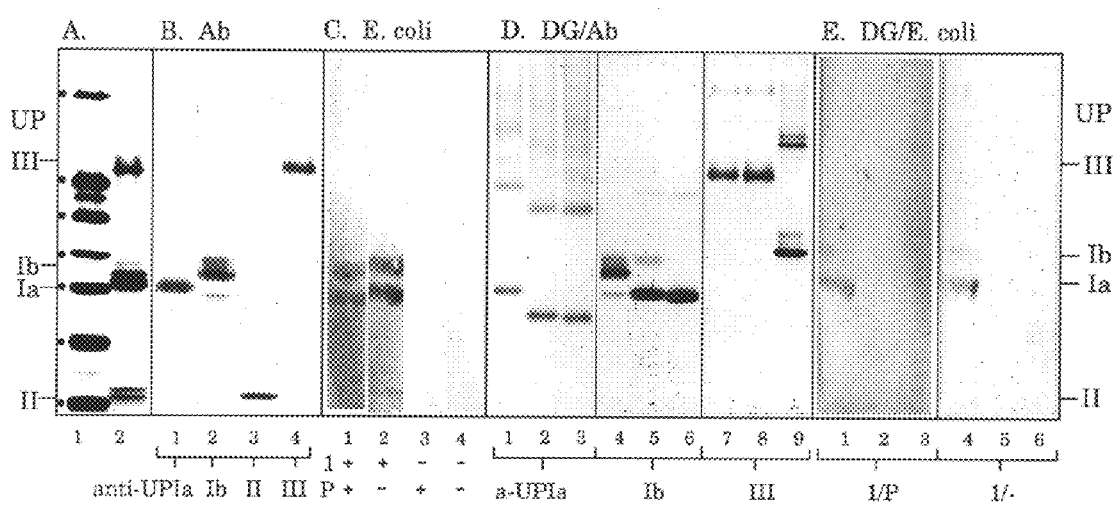
FIG. 5 provides a series of SDS-PAGE gels showing binding of type 1-fimbriated *E. coli* to asymmetric unit membrane protein subunits.

Results of assaying for binding of type-1 fimbriated E. coli to protein subunits of asymmetric unit membrane are shown in FIG. 5. More specifically, lane A shows the electrophoretic pattern of bovine urothelial plaques. Proteins of bovine asymmetric unit membranes were dissolved in 1% SDS, separated by SDS/PAGE, and visualized by silver-nitrate staining (lane 2). Three major protein bands were separated: the 47 kDa UPIII, the 27- to 28-kDa UPIa and UPIb, and the 15 kDa UPII. Lane 1 shows molecular weight markers dotted: 66, 45, 36, 29, 24, 20 and 14 kDa.

Lane B shows the identification of uroplakins by immunoblotting. For this procedure, uroplakins were electrophoretically transferred to nitrocellulose and immunoblotted using antibodies (Wu et al, 1994.) against synthetic peptides corresponding to UPIa (lane 1), UPIb (lane 2), UPII (lane 3), and UPIII (lane 4).

Lane C of FIG. 5 shows binding of E. coli to uroplakins. Uroplakins that had been electrophoretically transferred to nitrocellulose were incubated with radiolabeled E. coli strains that express (1) both type 1 and P fimbriae (strain J96); (2) type 1 only (SH48); (3) P only (HU849); or (4) none (P678-54). It should be noted that the type-1 expressing *E. coli* bind predominantly to UPIa and UPIb.

Lane D shows glycosylation of uroplakins. Bovine uroplakins were dissolved in 0.1% SDS, treated with a buffer as a control (lanes 1, 4 and 7), or endo H to remove the high mannose type of sugars (lanes 2, 5 and 8), or endo F (lanes 3, 6 and 9). The uroplakins were then resolved by SDS/PAGE and immunoblotted using antibodies to uroplakins as indicated. It should be noted that endo H removed approximately 3 kDa equivalents of the high-mannose type of sugars from UPIa and UPIb. Endo F removed approximately 20 kDa equivalents of sugars, most likely the complex type, from UPIII. As shown earlier, incubation of SDS-dissolved UPIa (overnight at 37° C.) resulted in oligomerization (Wu et al., 1995). However, very little of these oligomers are present in the asymmetrical unit membrane fraction used in bacterial binding assays (cf. B, lane 1).

Lane E shows *E. coli* binding to deglycosylated uroplakins. Uroplakins that had been treated with buffer (controls, lanes 1 and 4), endo H (lanes 2 and 5), or endo F (lanes 3 and 6) were transferred to nitrocellulose and incubated with radiolabeled *E. coli* expressing both type 1 and P fimbriae (1/P; strain J96) or type 1 only (1/–; SH48) as indicated. The binding of type-1 fimbriated bacteria to UPIa and UPIb was abolished by endo H and endo F treatment, suggesting the involvement of high-mannose type sugars in the binding.

Unique Features of the Uroplakin I Receptors

Although existing data strongly suggest that type 1 fimbriae play an important role in many infections, their urothelial receptors have so far been elusive. The present invention provides the first evidence that uroplakin Ia and uroplakin Ib, two major glycoproteins of asymmetric unit membrane plaques covering >70% of the urothelial apical surface, can serve as receptors for type 1-fimbriated microorganisms. These uroplakin receptors have several interesting properties. First, uroplakin Ia and uroplakin Ib, two closely related isoforms sharing 39% amino acid sequences, belong to a novel family of integral membrane proteins, all having four transmembrane domains. Members of this gene family include several important leukocyte differentiation-related surface antigens (CD9, CD37, and CD53), a tumor-associated antigen (CD63), a prostate tumor metastasis suppressor gene (CD82/KAI1), and two Schistosoma antigens. Second, they form together with uroplakin II and uroplakin III, 16-nm luminal protein particles that are arranged in two-dimensional crystalline arrays. Image processing revealed that each 16-nm particle consists of six inner and six outer subdomains interconnected, forming a continuous strand in the shape of a twisted ribbon. As part of such a highly organized structure, which can be readily isolated in milligram quantities, uroplakin I proteins are uniquely suitable for detailed structural analysis, both for their protein backbones and their sugar moieties. Third, consistent with the fact that asymmetric unit membranaceum is a hallmark of differentiated urothelial umbrella cells, uroplakins, as the major asymmetric unit membrane subunits, are urothelium-specific and differentiation-dependent. Thus, uroplakins are found so far only in the differentiated urothelial cells. Finally, it has been demonstrated that uroplakin I proteins, like uroplakin II and uroplakin III, are highly conserved during mammalian evolution, since it was found that the uroplakins of nine mammalian species, including bovine and human, showed similar sizes, antigenicities, and in some cases, amino acid sequences (Wu et al., 1994). The present finding that type 1-fimbriated *E. coli* can bind with similar facility to asymmetric membrane units of bovine, human, monkey and mouse extends this conservation to include the terminal mannose moieties recognizable by the adhesin of type 1 fimbriae, i.e., the FimH. This observation makes it possible to use asymmetric unit membranes from mammals other than humans, which are available in large quantities, as a physiologically relevant and convenient system for studying the molecular details of, and for screening drugs that can interfere with, the interactions between type 1 adhesin and its receptors in humans.

Sequencing of Uroplakin Ia and Uroplakin Ib Amino Acid Sequencing

Bovine asymmetric unit membranes were purified by sucrose density gradient centrifugation as described by Wu et al., 1990. The asymmetric unit membrane protein components, without prior reduction, were separated by SDS-PAGE, 15% acrylamide, and then transferred electrophoretically to Immobilon-PVDF membrane (Millipore, Bedford, Mass.) and stained with Coomassie blue. The 27- to 28-kDa protein band corresponding to uroplakin I was excised and subjected to $NH_2$-terminal amino acid sequencing. For generating internal sequences the electrophoretically purified 27- to 28-kDa protein was digested by cyanogen bromide or trypsin. The cyanogen bromide-peptide fragments were resolved by SDS-PAGE (16.5% acrylamide, 6% bisacrylamide) in a Tricine buffer, while the tryptic peptides were fractionated by reverse phase HPLC. The $NH_2$-terminal sequences of all of the major, well-resolved peptide bands or peaks were determined.

Automatic amino acid sequencing was performed using an ABI model 477A protein sequencer.

Polymerase Chain Reaction and Screening of cDNA Library

Total RNAs were isolated from bovine tissues and cultured bovine urothelial cells, and poly(A)+mRNAs were purified using an oligo-dT cellulose column (type 3;

Collaborative Research, Boston, Mass.). Single-stranded cDNAs of these mRNA were synthesized using avian myoblastosis virus reverse transcriptase and oligo-dT primers. Degenerate oligo nucleotide primers in both sense and antisense orientations were synthesized based on three partial amino acid sequences: PEVVFP, MLTFYS, and DYLFTK. To facilitate the subcloning of the PCR products, additional HindIII and EcoRI linkers were placed on the 5'-end of the sense and antisense primers, respectively. Polymerase chain reactions were performed with Taq polymerase using bovine liver or bladder epithelial single-stranded cDNA as the template. Thirty thermal cycles were performed, each consisting of denaturation at 94° C. for one minute, annealing at 55° C. for one minute, and extension at 72° C. for one minute. The PCR products were resolved in a 1.5% agarose gel. Selected bands were eluted, subcloned into pGEM-72 and sequenced using a T7 DNA Sequencing Kit. Specific PCR products were $^{32}P$-labeled and used to screen a λgt11 cDNA library of bovine bladder epithelium. Hybridization was carried out at 60° C. overnight in a solution containing 6×SSC, 5×Denhardt's solution, 1% SDS, and 100 micrograms/ml of denatured salmon sperm DNA. cDNA inserts from positive phage were subcloned into pGEM7Z and sequenced. The immunological screening of a lambda/gt 11 expression library was done according to standard methods. The cDNA inserts of positive clones were subcloned into pGEM3Z and sequenced in both strands.

Generation of Antibodies Against Synthetic Peptides

Two peptides, DSNQGRELTRLWDR (amino acids 139–152 of SEQ ID NO:13) and AKDDSTVR

SFQGLLIFGN (SEQ ID NO:16), were chemically synthesized based on the cDNA-derived amino acid sequences of uroplakin Ia and uroplakin Ib, respectively. An additional cysteine residue was placed at the COOH terminus of each peptide to facilitate the conjugation to the carrier proteins. The underlined serine residue of the uroplakin Ib peptide replaced an original cysteine to avoid excessive cross-linking. These two peptides were cross linked to keyhole limpet hemocyanin or bovine serum albumin using maleimidobenzol-N-hydroxysuccinimide. One hundred micrograms of the conjugated peptide were used to immunize each rabbit for the primary injection, and 50 micrograms for booster injections at two week intervals.

Sequence Analysis

The nucleotide and the deduced amino acid sequences of uroplakin Ia and uroplakin Ib were compared with the entire GenBank, EMBL, PIR-Protein, and SwissProt data bases though FASTA or TFASTA algorithms (GCG7 package). The secondary structures of proteins were predicted by the PEPTIDESTRUCTURE program or GeneWorks 2.0. Multiple sequence alignment was carried out using the LINEUP and PILEUP programs.

FIG. 6 shows the partial amino acid sequences of bovine 27- to 28-kDa uroplakin Ia. FIG. 6A shows the primary data showing the original partial amino acid sequences generated by automatic sequencer. C1 (SEQ ID NO:1) and C2 (SEQ ID NO:2) are the $NH_2$-terminal sequences of two cyanogen bromide-peptides; T1 (SEQ ID NO:3) and T2 (SEQ ID NO:4) are $NH_2$-terminal sequences of two tryptic peptides, while $NH_2$ (SEQ ID NO:5) represents the $NH_2$-terminal sequences of electrophoretically purified, intact 27- to 28-kDa proteins.

All amino acids are represented by standard single letter codes. In many cases two amino acids were identified from one cycle of Edman sequencing; these two amino acids are listed in parentheses.

In FIG. 6B, the amino acid residues shared by C1 and C2 peptides, and the remaining COOH-terminal C2 sequence, are shown as #1 sequence (SEQ ID NO:6). Subtraction of this sequence from C1 and C2 sequences yielded the #2 (SEQ ID NO:7) and #3 (SEQ ID NO:8) sequence, respectively. Amino acids shared by T1 and T2, as well as the #2 sequence, are listed as #4 sequence (SEQ ID NO:9). Subtraction of this sequence from T1 and T2 sequences gave rise to #5 (SEQ ID NO:10) and #6 (SEQ ID NO:11) sequences, respectively. From the three underlined sequences, 1 to 3, degenerate oligonucleotide primers were synthesized in both sense and antisense directions and were used to amplify the cDNAs of uroplakin I by PCR.

FIG. 7 shows the deoxynucleotide (SEQ ID NO:12) and deduced amino acid sequence (SEQ ID NO:13) of bovine uroplakin Ia. The stretches of deduced amino acid sequences which match with protein micro-sequencing data are underlined and numbered according to FIG. 6; inconsistencies are underlined by dashes. Four stretches of hydrophobic amino acids that are long enough to span the lipid bilayer are boxed and shaded. A potential N-linked glycosylation site is circled, and the polyadenylation signal near the poly(A) tail is underlined by a thick bar.

FIG. 8 shows the deoxynucleotide (SEQ ID NO:14) and deduced amino acid sequence (SEQ ID NO:15) of bovine uroplakin Ib. The deduced $NH_2$-terminal amino acid sequence, which is underlined, matches one of the two $NH_2$-terminal sequences of 27- to 28-kDa uroplakin I. The N-linked glycosylation site is circled, and the putative polyadenylation signal AATAAA SEQ is underlined by a thick bar. The dash-underlined 3'-untranslated region represents a bovine Alu-like repetitive sequence. The other symbols are as in FIG. 7.

Possible Roles of Type 1 and P Fimbriae in Urinary Tract Infections: Cooperativity and Selection The results described above demonstrated that the FimH adhesin of type 1 fimbriae, but not the three major G adhesins of the P fimbriae, were able to bind asymmetric unit membranes. This suggests that type 1 and P fimbriae may play different roles in various stages of bacterial infection by recognizing distinct receptors, i.e., the urothelial uroplakin I proteins and kidney glycolipids, respectively. In a relatively early phase of urinary tract infection, *E. coli* has to attach to urothelial surface in the bladder, most likely via type 1 fimbriae-uroplakin I interactions. This allows the bacteria to colonize to maintain a sufficient number of infectious agents, possibly causing cystitis. Moreover, since the uroplakin I-containing urothelium covers almost the entire urinary tract, this provides a mechanism allowing the type 1-fimbriated *E. coli* to ascend through the ureter, against the urine flow, to invade the kidneys. Once reaching the kidney, P fimbriae may then take over as the primary mediator of bacterial attachment, via their binding to the glycolipid receptors. This scheme emphasizes the cooperative relationship between the type 1 and P fimbriae in kidney infection (pyelonephritis), and suggests a selection mechanism that explains why a great majority of urinary infection isolates are type 1-fimbriated and why most *E. coli* isolates from pyelonephritis patents are in addition P-fimbriated.

Blocking Bacterial Binding to Urothelial Receptors by Urinary Soluble Proteins and Mucus: A Host Defense Mechanism Although type 1 fimbriae are known to be able to recognize several nonurothelial molecules, including a 65-kda uroplakin I protein of guinea pig erythrocytes, leukocyte adhesion molecules CD11 and CD18, laminin, fibronectin, and uromodulin, these molecules are not present on the urothelial surface and, therefore, clearly cannot be the urothelial receptors of the bacteria. However, uromodulin, also known as the Tamm-Horsfall protein, a kidney-derived, mannosylated protein present in an extraordinarily high concentration in the urine (20 to 30 mg/liter), may play a defensive role. It can saturate all of the mannose-binding sites of the type 1 fimbriae, thus potentially blocking bacterial binding to the uroplakin I receptors of the urothelium. Another possible defense mechanism involves the mucus layer that coats the urothelial surface. It has been demonstrated in animal models that type 1-fimbriated *E. coli* cannot bind to normal bladder surface that is covered by an intact mucus layer. Damage of the mucus layer allows the bacteria to gain access, however, to the receptors of the underlying urothelium, thus allowing adherence. Defects in these defense mechanisms, which entail the combined effects of the soluble uromodulin and the urothelial mucus, may lead to the adherence of *E. coli*, via FimH-uroplakin I receptor interactions, to urothelial surface, thus setting the stage for urinary tract infections.

Soluble urinary proteins and insoluble urinary mucus components regulate the in vivo binding of type 1-fimbriated microorganisms to the uroplakin I receptors. Differences in uroplakin I expression may contribute to different susceptibility of individuals to urinary tract infections, as differences in receptor concentrations lead to differing amount of adhesion of microorganisms to the receptors.

Since the present disclosure enables a person to isolate homologues of uroplakins as described herein, and since such homologues can be sequenced by standard techniques, and since such amino acid sequences can be converted to the nucleotide sequences that code for them, one can thus construct DNA molecules that are homologues of DNA molecules defined herein. Such DNA molecules are equivalents of these described herein because they are used in substantially the same way and for substantially the same purpose.

Since the amino acid sequences of bovine uroplakin Ia and uroplakin Ib are known, it is possible to prepare functional derivatives of these uroplakins as well as uroplakins II and III. By "functional derivative" is meant a fragment, variant, analog or chemical derivative of the subject uroplakin, which terms are defined below. A functional derivative retains at least a portion of the amino acid sequence of the uroplakin of interest which permits its utility in accordance with the present invention, namely, attachment of type 1 fimbriae thereto. These functional derivatives bind type 1 fimbriae of microorganisms.

A "fragment" of a uroplakin refers to any subset of the molecule, that is, a shorter peptide. Fragments of interest are those to which type 1 fimbriae attach.

A "variant" of a uroplakin refers to a molecule which is substantially similar to either the entire peptide or a fragment thereof. Variant peptides may be conveniently prepared by direct chemical synthesis of the variant peptide, using methods well known in the art.

Alternatively, amino acid sequence variants of the uroplakins can be prepared by mutations in the DNAs which encode the synthesized uroplakins. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produced secondary mRNA structure (cf. European Patent Publication No. EP 75,444).

At the genetic level, these variants ordinarily are prepared by site-directed mutagenesis (as exemplified by Adelman et al., *DNA* 2:183 (1983) of nucleotides in the DNA encoding the peptide molecule, thereby producing DNA encoding the variant, and thereafter expressing the DNA in suitable recombinant cell culture allowing the biosynthesis of proteins with proper glycosylation and other secondary modifications. The variants typically exhibit the same qualitative biological activity as the nonvariant peptide.

An "analog" of a uroplakin refers to a non-natural molecule substantially similar to either the entire molecule or a fragment thereof.

A "chemical derivative" of a uroplakin contains additional chemical moieties not normally part of the uroplakin amino acid sequence. Covalent modifications of the amino acid sequence are included within the scope of this invention. Such modifications may be introduced into the uroplakin by reacting targeted amino acid residues of the peptide with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidazoyl)propionic acid, chloroacetyl phosphate, alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2, 4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and 3-nitro derivatives, respectively.

Carboxyl side groups (aspartyl or glutamyl) are selectively modified by reaction with carbodiimides (R'-N-C-N-R') such as 1-cyclohexyl-3-[2-morpholinyl-(4-ethyl)] carbodiimide or 1-ethyl-3-(4-azonia-4,4-dimethlypentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Inhibiting Binding of Type 1 Fimbriae-Expressing Bacteria to Uroplakins

Type 1 fimbriated-bacteria can be prevented from attaching to the bacterial binding site of uroplakin Ia or uroplakin Ib by the soluble form of the bacterial-binding site, antibodies against the bacterial-binding site, antibodies against the bacterial-binding site of the adhesin, and antireceptor antibodies that occupy the bacterial site or soluble adhesins.

Soluble Form of the Bacterial-Binding Site

The soluble variants or derivatives of the bacterial binding site uroplakin Ia or uroplakin Ib can be administered to a patient to inhibit or prevent attachment of type 1 fimbriae-expressing bacteria to the bacterial binding sites on uroplakin Ia or uroplakin Ib. The soluble form of the bacterial-binding site, its active mutants, fused proteins, and their salts, functional derivatives and active fractions, can be used as active ingredients of pharmaceutical compositions to protect mammals against infections by type 1 fimbriae-expressing bacteria. The soluble variants or derivatives of the uroplakin Ia or uroplakin Ib bacterial binding site can also be used to treat cells in mammals against infection by type 1 fimbriae-expressing bacteria by administering an antibacterial effective amount of a pharmaceutical composition comprising a soluble variant or derivatives of the uroplakin Ia or uroplakin Ib bacterial binding site or the uroplakin.

The soluble variant or derivative of the uroplakin Ia or uroplakin Ib receptor can be obtained by isolating uroplakin Ia or uroplakin Ib and isolating and/or purifying soluble variants of the uroplakin Ia or uroplakin Ib bacterial binding sites by chromatography, including immunochromatography using monoclonal antibodies specific for an epitope of a soluble uroplakin Ia or uroplakin Ib receptor protein.

Alternatively, isolation and/or purification of soluble variants or derivatives of uroplakin Ia or uroplakin Ib bacterial binding sites from asymmetric unit membrane or from a mixture of the uroplakins themselves may comprise (1) solubilizing the asymmetric unit membrane using a detergent such as octyl glucoside; (2) generating soluble derivatives or fragments of UPIa and UPIb using cyanogen bromide or proteolytic enzymes; (3) concentrating the fluid sample by microfiltration and/or ultrafiltration; (4) affinity chromatography using monoclonal antibodies specific for soluble uroplakin Ia or uroplakin Ib receptor; (5) reverse phase HPLC; and/or optionally, (6) size exclusion chromatography in order to isolate the soluble uroplakin Ia or uroplakin Ib receptor. In the above method, step (6) is optional, since the fraction obtained after the reverse phase HPLC step may be of sufficient purity.

Preferably in all steps of the purification, the soluble uroplakin Ia or uroplakin Ib receptor fractions are monitored by measuring the antibacterial activity, i.e., by measuring the inhibition of attachment of labelled type 1 fimbriae-expressing bacteria to the soluble receptor fractions.

Soluble variants or derivatives of uroplakin Ia or uroplakin Ib receptors can be used according to known method steps to provide purified soluble variants or derivatives of the uroplakin Ia or uroplakin Ib, which can then be sequenced. In a preferred embodiment, the soluble variants or derivatives of the uroplakin Ia or uroplakin Ib bacterial binding sites are absorbed on a PVDF membrane and subjected to micro sequence analysis on a protein micro sequences, as commercially available, and/or by techniques known to those skilled in the art.

As used herein, the term "muteins" refers to analogues of the soluble uroplakin Ia or uroplakin Ib binding site or of uromodulin in which one or more of the amino acid residues of the natural soluble uroplakin Ia or uroplakin Ib binding site or uruomodulin, preferably 1–10 and more preferably 1–5 residues, or even only a single residue, are replaced by different amino acid residues or are deleted, or one or more amino acid residues, such as 1–10, 1–5 or only one residue are added to the natural sequence of the soluble uroplakin Ia or uroplakin Ib binding site or to uromodulin, without substantially changing the antibacterial activity of the resulting product. These muteins are prepared by known synthesis and/or site-directed mutagenesis techniques, or by any other known technique suitable therefor. The substitutions are preferably conservative. See., e.g., Schulz, G. E. et al., *Principles of Protein Structure*, Springer-Verlag, New York, 1978, and Creighton, T. E., *Proteins: Structure and Molecular Properties*. W. H. Freeman & Co., San Francisco, 1983, which are hereby incorporated by reference.

The types of such substitutions which may be made in the protein or peptide molecules of the present invention may be based on analysis of the frequencies of amino acid changes between a homologous protein of different species, such as those presented in Table 1–2 of Schulz et al. (supra) and FIGS. 3–9 of Creighton (supra). Based upon such analysis, conservative substitutions may be defined herein as exchanges within one of the following five groups:

1. Small aliphatic, nonpolar or slightly polar residues: ala, ser, thr (pro, gly);

2. Polar, negatively charged residues and their amides: asp, asn, glu, gly;

3. Polar, positively charged residues: his, arg, lys;

4. Large aliphatic, nonpolar residues: met, leu, ile, val (cys); and

5. Large aromatic residues: phe, tyr, trp.

The three amino acid residues in parentheses above have special roles in protein architecture. Gly is the only residue lacking any side chain, and thus imparts flexibility to the chain. Pro, because of its unusual geometry, tightly constrains the chain. Cys can participate in disulfide bond formation which is important in protein folding. Note that Schulz et al. would merge Groups 1 and 2, above. Note also that Tyr, because of its hydrogen bonding potential, has some kinship with Ser, Thr, etc.

Conservative amino acid substitutions according to the present invention, e.g., as presented above, are known in the art and would be expected to maintain biological and structural properties of the polypeptide after amino acid substitution. Most deletions and insertions, and substitutions according to the present invention, are those which do not produce radical changes in the characteristics of the protein or peptide molecules. One skilled in the art will appreciate that the effect of substitutions can be evaluated by routine screening assays, either immunoassays or bioassays. For example, a mutant typically is made by site-specific mutagenesis of the peptide molecule-encoding nucleic acid, expression of the mutant nucleic acid in recombinant cell culture, and, optionally, purification from the cell culture, or a biological sample containing a soluble uroplakin Ia or uroplakin Ib receptor protein, for example, by immunoaffinity chromatography using a specific antibody on a column to absorb the mutant by binding to at least one epitope.

Preferably, the synonymous amino acid groups are those defined in Table 3. More preferably, the synonymous amino acid groups are those defined in Table 4; and most preferably, the synonymous amino acid groups are those defined in Table 5.

TABLE 3

Preferred Groups of Synonymous Amino Acids

| Amino Acid | Synonymous Group |
| --- | --- |
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| MetTrp | Phe, Ile, Val, Leu, MetTrp |

TABLE 4

More Preferred Groups of Synonymous Amino Acids

| Amino Acid | Synonymous Group |
| --- | --- |
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| MetTrp | Met, Phe, Ile, Val, LeuTrp |

TABLE 5

Most Preferred Groups of Synonymous Amino Acids

| Amino Acid | Synonymous Group |
| --- | --- |
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| MetTrp | Met, Ile, LeuMet |

Any analogous mutein preferably has a sequence of amino acids sufficiently duplicative of those of uroplakin Ia or uroplakin Ib soluble bacterial binding sites or of the ability of uromodulin to inhibit binding, such as to have substantially similar activity to uroplakin Ia or uroplakin Ib soluble bacterial binding sites or to uromodulin, respectively. One activity of soluble uroplakin Ia or uroplakin Ib bacterial binding sites is their capability to bind to bacteria which express type 1 fimbriae. As long as the mutein has substantial attachment to one or more of such bacteria, it can be used in the purification of such receptors, such as by means of affinity chromatography. Thus, it can be determined whether any given mutein has substantially the same activity as uroplakin Ia or uroplakin Ib bacterial binding sites by means of routine experimentation. In a similar fashion, any mutein of uromodulin can be readily tested to determine if the mutein inhibits binding of type 1 fimbriae to uroplakin Ia and/or uroplakin Ib.

In a preferred embodiment, any such mutein has at least 40% identity or homology with the sequence of either uroplakin Ia or uroplakin Ib bacterial binding sites. More preferably, it has at least 50%, at least 60%, at least 70%, at least 80%, or, most preferably, at least 90% identity or homology thereto.

Examples of production of amino acid substitutions in proteins which can be used for obtaining muteins of uroplakin Ia or uroplakin Ib bacterial binding sites or proteins or their active fractions for use in the present invention include any known method steps, such as presented in U.S. Pat. Nos. Re 33,653, 4,949,314, 4,588,585 and 4,737,462 to Mark et al; U.S. Pat. No. 5,116,943 to Koths et al.; U.S. Pat. No. 4,965,195 to Namen et al.; U.S. Pat. No. 4,879,111 to Chong et al; and U.S. Pat. No. 5,017,691 to Lee et al.; as well as lysine substituted proteins presented in U.S. Pat. No. 4,904,584 to Shaw et al. All of these patents are hereby incorporated by reference in their entirety.

The term "fused protein" refers to a polypeptide comprising a soluble form of a uroplakin Ia or Ib bacterial binding site or a mutein thereof fused with another protein which has an extended residence time in the body fluids. The soluble form of the uroplakin Ia or uroplakin Ib bacterial binding site may thus be fused to another protein, polypeptide or the like, e.g., an immunoglobulin or fragment thereof.

The term "salts" herein refers to both salts of carboxyl groups and to acid addition salts of amino groups of the soluble uroplakin Ia or uroplakin Ib receptor, muteins, and fused proteins thereof. Salts of a carboxyl group may be formed by means known in the art and include inorganic salts, for example, sodium, calcium ammonium, ferric or zinc salts and the like, and salts with organic bases such as those formed with amines such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid.

"Functional derivatives" as used herein covers derivatives of the soluble uroplakin Ia or uroplakin Ib bacterial binding site and their fused proteins and muteins, which may be prepared from the functional groups which occur as side chains on the residues or the—or C-terminal groups, by means known in the art, and are included in the invention as long as they remain pharmaceutically acceptable, i.e., they do not destroy the activity of the protein and do not confer toxic properties on compositions containing it. These derivatives may, for example, include polyethylene glycol side chains which may mask antigenic sites and extend the residence time of the soluble uroplakin Ia or uroplakin Ib receptor in body fluids. Other derivatives include aliphatic esters of the carboxy groups, amides of the carboxy groups by reaction with ammonia or with primary or secondary amines, N-acyl derivatives of free amino groups of the amino acid residues formed with acyl moieties (e.g., alkanoyl or carbocyclic aroyl groups) or acyl derivatives of free hydroxyl groups (for example, that of seryl or threonyl residues) formed with acyl moieties. The term "functional derivative" also includes proteins which have an amino acid sequence longer or shorter than the sequence determined, as long as the protein still has the ability to inhibit viral infection.

As "active fractions" of the soluble uroplakin Ia or uroplakin Ib bacterial binding sites, their fused proteins and their muteins, the present invention covers and fragment or precursors of the polypeptide chain of the protein molecule alone or together with associated molecules or residues linked thereto, e.g., sugar or phosphate residues, or aggregates of the protein molecule or the sugar residues by themselves, provided said fraction has the ability to inhibit attachment to the receptors by type 1 fimbriae-expressing bacteria. Such active fractions can be readily determined by testing smaller and smaller portions of the entire soluble form of the uroplakin Ia or uroplakin Ib bacterial binding site or mutein to find the smallest fragment that retains the ability to inhibit attachment to the bacterial binding site by type 1 fimbriae-expressing bacteria. Undue experimentation would not be involved, as the required tests for inhibition of attachment to the bacterial binding sites by type 1 fimbriae-expressing bacteria as described herein may be routinely carried out.

The present invention further concerns DNA molecules comprising the nucleotide sequence encoding the soluble forms of the uroplakin Ia or uroplakin Ib bacterial binding sites, fused proteins, muteins, or active fractions thereof, replicable expression vehicles containing said DNA molecules, hosts transformed therewith and protein produced by expression of such transformed hosts. The term "DNA molecules" includes genomic DNA, cDNA, synthetic DNA and combinations thereof.

In order to be capable of expressing the soluble form of the uroplakin Ia or uroplakin Ib bacterial binding sites, their muteins or the fused proteins, an expression vector should comprise also specific nucleotide sequences containing transcriptional and translational regulator information linked to the DNA coding for the desired protein in such a way as to permit gene expression and production of the protein. First, in order for the gene to be transcribed, it must be preceded by a promoter recognizable by RNA polymerase, to which the polymerase binds and thus initiates the transcription process. There are a variety of such promoters in use, which work with different efficiencies (strong and weak promoters). They are different for prokaryotic and eukaryotic cells.

The promoters that can be used in the present invention may be either constitutive, for example, the int 1–5 promoter of bacteriophage lambda, the bla promoter of the β-lactamase gene or pBR322, and the CAT promoter of the chloramphenicol acetyl transferase gene of pPR325, etc., or inducible, such as the prokaryotic promoters including the major right and left promoters of bacteriophage lambda ($P_l$ and $P_r$), the try, recA, lacZ, lacI, ompF and gal promoters of *E. coli* or the trp-lac hybrid promoter, etc. [Glick, B. R., (1987) *J. Ind. Microbiol.* 1:277–282].

Besides the use of strong promoters to generate large quantities of mRNA, in order to achieve high levels of gene expression in prokaryotic cells, it is necessary to use also ribosome-binding sites to ensure that the mRNA is efficiently translated. One example is the Shine-Dalgarno sequence (SD sequence) appropriately positioned from the initiation codon and complementary to the 3'-terminal sequences of 16S RNA.

For eukaryotic hosts, different transcriptional and translational regulator sequences may be employed, depending on the nature of the host. They may be derived from viral sources, such as adenovirus, bovine papilloma virus, Simian virus, or the like, where the regulatory signals are associated with a particular gene which has a high level of expression. Examples are the TK promoter of Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for the soluble uroplakin Ia or uroplakin Ib receptor of the invention or its fragments or muteins or fused proteins thereof, and the operably linked transcriptional and translational regulator signals, is inserted into a vector which is capable of integrating the desired gene sequences into the host cell chromosome. In order to be able to select the cells which have stably integrated the introduced DNA into their chromosomes, one or more markers which allow for selection of host calls which contain the expression vector is used. The marker may provide for prototropy to an auxotrophic host, resistance, e.g., to antibiotics, or heavy metals, such as copper, or the like. The selectable marker gene can either be directly linked to the DNA gene sequences to be expressed, or introduced into the same cell by cotransfection. Additional elements may also be needed for optimal synthesis of single chain binding protein mRNA. These elements may include splice signals as well as transcription promoters, enhancers, and termination signals. cDNA expression vectors incorporating such element include those described by Okayama, H., (1983) *Mol Cel. Biol.* 3:280.

In a preferred embodiment, the introduced DNA molecule will be incorporated into a plasmid or viral vector capable of automonomous replication in the recipient host. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli*, for example pBR322, ColE1, pSC101, pACYC 184, etc. cf. Maniatis et al., op. cit.); Bacillus plasmids such as pC194, pC221, pT127, etc (Gryczan, T., "The Molecular Biology of the Bacilli", Academic Press, NY (1982), pp. 307–329); Streptomyces plasmids including pIJ101 (Kendall, K. J. et al., (1987) *J. Bacteriol.* 169:4177–4183); Streptomyces bacteriophages such as φC31 (Chater, K. F. et al., in "Sixth International Symposium on Actinomycetales Biology", Akademiai Kaido, Budapest, Hungary (1986), pp. 45–54; and Pseudomonas plasmids (John, J. F. et al., (1986) *Rev. Infect. Dis.* 8: 693–704) and Izaki, K. (1978) *Jpn. J. Bacteriol.* 33:729–742).

Preferred eukaryotic plasmids include BPV, vaccinia, SV40, 2-micron circle, etc., or their derivatives. Such plasmids are well known in the art (Botstein, D. et al. (1982) *Miami Wint. Symp.* 19:265–274; Broach, J R, in "The Molecular Biology of the Yeast Saccharomyces: Life Cycle and Inheritance", Cold Spring Harbor Laboratory, Cold Spring Harbor, N.Y., pp. 445–470 (1981); Broach, J. R. (1982) *Cell* 28:203–204; Bololon, D. P., et al., (1980) *J. Clin. Hematol. Oncol.* 10:39–48; Maniatis, T., in "Cell Biology: A Comprehensive Treatise, vol. 3: Gene Expression," Academic Press, NY, pp. 563–608).

Once the vector or DNA sequence containing the construct(s) has been prepared for expression, the expression vector may be introduced into an appropriate host cell by any variety of suitable means, such as transformation, transfection, lipofection, conjugation, protoplast fusion, electroporation, calcium phosphate precipitation, direct microinjection, etc.

Host cells to be used in this invention may be either prokaryotic or eukaryotic. Preferred prokaryotic hosts include bacteria such as *E. coli*, Bacillus, Streptomyces, Pseudomonas, Salmonella, Serratia, etc. The most preferred prokaryotic host is *E. coli*. Of course, the prokaryotic host must be compatible with the replicon and control sequences in the expression plasmid.

Because the soluble forms of the uroplakin Ia and uroplakin Ib bacterial binding sites are glycosylated, evkaryotic hosts are preferred over prokaryotic hosts. Preferred eukaryotic hosts are mammalian cells, e.g., human, monkey, mouse and Chinese hamster ovary (CHO) cells, because they provide post-translational modifications to protein molecules including correct folding, correct disulfide bond formation as well as glycosylation at the correct sites. Also, yeast cells and insect cells can carry out post-translational peptide modifications including high mannose glycosylation. A number of recombinant DNA strategies exist which utilize strong promoter sequences and high copy number of plasmids which can be utilized for production of the desired proteins in yeast and in insect cells. Yeast cells recognize leader sequences on cloned mammalian gene products and secrete peptides bearing leader sequences.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to shuttle the vector between host cells of different species. After the introduction of the vector, the host cells are grown in a selective medium, which selects for the growth of vector-containing cells. Expression of the cloned gene sequence(s) results in the production of the soluble form of the uroplakin Ia or uroplakin Ib bacterial binding site, a fusion protein, or a mutein or a fragment thereof. The expressed protein is then isolated and purified by any conventional procedure involving extraction, precipitation, chromatography, electrophoresis, or the like, or by affinity chromatography, using anti-soluble uroplakin Ia or uroplakin Ib bacterial binding site monoclonal antibodies immobilized on a gel matrix contained within a column. Crude preparations containing said recombinant soluble uroplakin Ia or uroplakin Ib bacterial binding site will be bound to the column by the specific antibody, while the impurities will pass through.

After washing, the protein is eluted from the gel at a high pH, e.g., pH 11.

The soluble uroplakin Ia or uroplakin Ib bacterial binding sites and their muteins, fused proteins and their salts, functional derivatives, and active fractions thereof are indicated for the treatment of infections in mammals of bacteria expressing type 1 fimbriae.

The present invention further relates to pharmaceutical compositions comprising a pharmaceutically acceptable carrier and the soluble forms of the uroplakin Ia and/or uroplakin Ib bacterial binding sites of the invention, or at least one of their active muteins, fused proteins and their salts, functional derivatives or active fractions thereof, either as the sole active ingredient or in combination with other antibacterial agents. These compositions may be used against infections of type 1 fimbriae-expressing bacteria. The mode of administration can be any accepted mode of administration for similar agents, and will depend on the condition to be treated, e.g., by direct introduction to the bladder via catheter or intramuscularly or subcutaneously, or by local injection or topical application in case of a localized infection, or continuously by infusion, etc.

The pharmaceutical compositions of the invention are prepared for administration by mixing the soluble forms of the uroplakin Ia and/or uroplakin Ib bacterial binding sites or their derivatives, alone or together with other antibacterial agents, with physiologically acceptable carriers, stabilizers and excipients, and prepared in dosage form, e.g., by lyophilization in dosage vials. The amount of active compound to be administered will depend on the route of administration, the disease to be treated, and the condition of the patient. Local injection, for instance, will require a lower amount of the protein on a body weight basis than will intravenous infusion in the case of systemic infection.

Effective amounts of a soluble form of the uroplakin Ia and/or uroplakin Ib bacterial binding site protein or composition are from about 0.01 μg to about 100 mg/kg body weight, and preferably from about 10 μg to about 50 mg/kg body weight. See, e.g., Berkow et al., eds., *The Merck Manual*, 16th edition, Merck and Co., Rahway, N.J., 1992; Goodman et al., eds., *Goodman and Gilman's The Pharmacological Basis of Therapeutics*, 8th edition, Pergamon Press, Inc., Elmsford, N.Y. (1990); *Avery's Drug Treatment: Principles and Practice of Clinical Pharmacology and Therapeutics*, 3rd edition, ADIS Press, LTD, Williams and Wilkins, Baltimore, Md. (1987), Ebadi, *Pharmacology*, Little, Brown and Co., Boston, (1985); Katzung, *Basic and Clinical Pharmacology*, Appleton and Lange, Norwalk, Conn. (1992), which references and references cited therein are entirely incorporated herein by reference.

Antibodies Against the Bacterial-Binding Site

Antibodies against the bacterial-binding site may be either polyclonal or monoclonal. They may be raised in rabbits, mice or other animals or tissue cultured cells derived therefrom, or can be products of cells or human origin. They may also be produced by recombinant DNA technology either in a form identical to that of the native antibody or as chimeric molecules, constructed by recombination of antibody molecules of human or animal origin or in other forms chosen to make the antibodies most suitable for use in therapy.

For preparation of the antibodies, either purified uroplakin Ia or uroplakin Ib, or at least one synthetic peptide identical to the known sequence or a fragment thereof, e.g., to the N-terminal protein sequence, may be used to immunize animals. A further possibility is to fuse one of the possible nucleotide sequences coding from a fragment of uroplakin Ia or uroplakin Ib to the gene coding for Protein A, to express the antibody. The antibody is then purified by affinity chromatography on a Sepharose column and then used to immunize animals.

The monoclonal antibodies of the present invention are prepared using conventional hybridoma techniques (Kohler et al., (1975) *Nature* 256:495; Kohler et al., (1976) *Eur. J. Immunol.* 6:511). After immunization, spleen cells alone or together with lymph node cells of the immunized animals are isolated and fused with a suitable myeloma cell line. After fusion, the resulting hybridoma cells are selectively maintained in HAT medium and then cloned. The hybridoma cells obtained through such as selection are then assayed to identify clones which secrete antibodies capable of binding uroplakin Ia or uroplakin Ib. After identification, the desired clones are grown in bulk, either in suspension culture or in ascitic fluid, by injection the cells into the peritoneum of suitable host mice. The monoclonal antibodies produced by the hybridomas are then isolated and purified. The monoclonal antibodies may also be immobilized and used for the purification of uroplakin Ia or uroplakin Ib in affinity purification procedures using an immunadsorbent column.

The term "antibody" is meant to include polyclonal antibodies, monoclonal antibodies, chimeric antibodies, anti-idiotypic antibodies to antibodies that can be labeled in soluble or bound form, as well as active fractions thereof provided by any known technique, such as, but not limited to, enzymatic cleavage, peptide synthesis, and recombinant techniques.

Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites.

Chimeric antibodies are molecules different portions of which are derived from different animal species, such as those having the variable region derived from a murine monoclonal antibody and a human immunoglobulin constant region. Chimeric antibodies are primarily used to reduce immunogenicity in application and to increase yields in production, for example, where murine monoclonal antibodies have high yields from hybridomas but higher immunogenicity in humans, such that human/murine chimeric monoclonal antibodies are used. Chimeric antibodies and methods for their productions are known in the art (Cabilly et al., *Proc. Natl. Acad. Sci. USA* 81:3273–3277 (1984); Morrison et al., *Proc. Natl. Acad. Sci. USA* 81:6851:6855 (1984); Boulilanne et al., *Nature* 312:643–646 (1984); Cabilly et al., European Patent Application 125023, published Nov. 14, 1984; Neuiberger et al., *Nature* 314:268–270 (1985); Taniguchi et al., European Patent application 171496 (published Feb. 19, 1985); Morrison et al., European Patent Application 173494 (published Mar. 5, 1986); Neuberger et al., PCT Application WO 8601533 (published Mar. 13, 1986); Kudo et al., European Patent Application 184187 (published Jun. 11, 1986); Sahagan et al., *J. Immunol.* 137:1066–1074 (1986); Robinson et al., International Patent Publication WO 9702671 (published May 7, 1987); Liu et al., *Proc. Natl. Acad., Sci. USA* 84:3439–3443 (1987); Sun et al., *Proc. Natl. Acad. Sci. USA* 84:214–218 (1987); Better et al., *Science* 240:1041–1043 (1988); and Harlow and Lane, ANTIBODIES: A LABORATORY MANUAL. These references are entirely incorporated herein by reference.

An anti-idiotypic antibody is an antibody which recognizes unique determinants generally associated with the antigen-binding site of an antibody. An anti-idiotypic antibody can be prepared by immunizing an animal of the same species and genetic type (e.g., a mouse strain) as the source of the monoclonal antibody with the monoclonal antibody to which an anti-idiotypic antibody is being prepared. The immunized animal will recognize and respond to the idiotypic determinants of the immunizing antibody by producing an antibody to these idiotypic determinants, i.e., the anti-idiotypic activity. See, for example, U.S. Pat. No. 4,699,880, the entire contents of which are hereby incorporated by reference.

Altering the glycosylation of the uroplakins can serve to inhibit attachment of bacteria expressing type 1-fimbriae.

The anti-idiotypic antibody may also be used as an immunogen to produce an immune response in yet another animal, producing a so-called anti-anti-idiotypic antibody. The anti-anti-idiotypic antibody may be epitopically identical to the original monoclonal antibody which induced the anti-idiotypic antibody. Thus, by using antibodies to the idiotypic determinants of a monoclonal antibody, it is possible to identify other clones expressing antibodies of identical specificity.

Accordingly, monoclonal antibodies generated against uroplakin Ia or uroplakin Ib, and related proteins of the present invention, may be used to induce anti-idiotypic antibodies in suitable animals, such as BALB/c mice. Spleen cells from such immunized mice are used to produce anti-idiotypic hybridomas secreting anti-idiotypic monoclonal antibodies. Further, the anti-idiotypic monoclonal antibodies can be coupled to a carrier such as keyhole limpet Hemocyanin (KPH) and used to immunize additional BALB.c mice. Sera from these mice will contain anti- anti-idiotypic antibodies that have the binding properties of the original monoclonal antibodies specific for uroplakin Ia or uroplakin Ib epitopes.

The term, "antibody" is also meant to include both intact molecules as well as active fractions thereof, such as, for example, Fab and F(ab')$_2$, which are capable of binding antigen. Fab and F(ab')$_2$ fragments lac the Fc fragment of intact antibody, clear more rapidly from the circulation, and may have less non-specific tissue binding than an intact antibody (Wahl et al., *J. Nucl. Med.* 24:316–325 (1983)).

Compositions according to the present invention are prepared for administration by mixing the antibody or its derivatives with physiologically acceptable carriers, stabilizer and excipients, and prepared in dosage form, e.g., by lyophilization in dosage vials. As with the soluble forms of the receptors, the amount of antibody to be administered will depend on the route of administration, the infection to be treated, and the condition of the patient.

For purposes of the present invention, "antibody" encompasses antibodies against the receptor-binding site, antibodies against the receptor-binding site of the adhesin, and antireceptor antibodies that occupy the receptor site or soluble adhesins.

The present invention also provides DNA molecules encoding any of the proteins of the present invention as defined above which are soluble receptors of uroplakin Ia or uroplakin Ib, their analogs, derivatives, and fragments; replicable expression vehicles comprising any such DNA molecules, host cells transformed with any such expression vehicles including prokaryotic and eukaryotic and host cells.

The present invention also includes a process for the production of any of the proteins of the present invention as defined above which are soluble forms of uroplakin Ia or uroplakin Ib receptors, their analogs, derivatives, and fragments by culturing a transformed cell in accordance with the present invention and recovering the protein encoded by the DNA molecule and the expression vehicle within such transformed host cell.

The present invention also provides DNA molecules encoding any of the proteins of the present invention as defined above which are soluble receptors of uroplakin Ia or uroplakin Ib, their analogs, derivatives, and fragments; replicable expression vehicles comprising any such DNA molecules, host cells transformed with any such expression vehicles including prokaryotic and eukaryotic and host cells.

The present invention also includes a process for the production of any of the proteins of the present invention as defined above which are soluble forms of uroplakin Ia or uroplakin Ib receptors, their analogs, derivatives, and fragments by culturing a transformed cell in accordance with the present invention and recovering the protein encoded by the DNA molecule and the expression vehicle within such transformed host cell.

The foregoing description of the specific embodiments will so fully reveal the general nature of the invention that others can, by applying current knowledge, readily modify and/or adapt for various application such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

All references cited in this specification are hereby incorporated by reference.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the Binvention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

REFERENCES

Eisenstein, B. I., "Type 1 Fimbriae of *Escherichia coli*: genetic regulation, morphogenesis, and Role in Pathogenesis," *Reviews of Infectious Diseases* 10 supplement; 2:s341–344, 1988.

Falkow, S. et al., "The Interaction of Bacteria with Mammalian Cells," [Review], *Annual Review of Cell Biology*, 8:333–63, 1992.

Foxman, B. et al., "Bacterial Virulence Characteristics of *Escherichia Coli* isolates from First-time Urinary Tract Infection," *Journal of Infectious Diseases*, 171:1514–21, 1995.

Fujita, K. et al., "In vitro Adherence of type 1-frimbriated uropathogenic *Escherichia coli* to Human Urethral Mucosa," [published erratum appears in *Infect Immun* 1990 Feb; 58(2):579]., *Infection & Immunity* 57:2574–9.

Hanson, M. et al., "Purification of the *Escherichia coli* Type 1 Pilin and Minor Pilus Proteins and Partial Characterization of the Adhesin Protein," *Journal of Bacteriology*, 170:3350–8, 1988.

Hoepelman, A. I. et al., "Consequences of Microbial Attachment: Directing Host Cell Functions with Adhesins," [Review], *Infection & Immunity*, 60;1729–33, 1992.

Hultgren, S. J. et al., "Pilus and Nonpilus Bacterial Adhesins: Assembly and Function in Cell Recognition," [Review], *Cell*, 73:887–901, 1993.

Hultgren, S. J. et al., "Role of Type 1 Pili and Effects of Phase Variation on Lower Urinary Tract Infections Produced by *Escherichia coli*," *Infection & Immunity*, 50:370–7, 1985.

Iwahi, T. et al., "Role of Type 1 Fimbraie in the Pathogenesis of Ascending Urinary Tract Infection Induced by *Escherichia coli* in Mice," *Infection & Immunity*, 39:1307–15, 1983.

Johanson, I. et al., "Roles of the Pap- and Prs-encoded Adhesins in *Escherichia coli* Adherence to Human Uroepithelial Cells," *Infection & Immunity*, 60:3416–22, 1992.

Jones et al., "FimH Adhesin of Type 1 Pili is Assembled into a Fibrillar Tip Structure In the Enterobacteriaceae," *Proceedings of the National Academy of Sciences of the United States of America*, 92:2081–5, 1995.

Keith, B. R. et al., "Receptor-binding Function of Type 1 Pili Effects Bladder Colonization by a Clinical Isolate of *Escherichia coli*," *Infection & Immunity*, 53:693–6, 1986.

Kisielius, P. V. et al., "In vivo Expression and Variation of *Escherichia coli* Type 1 and P Pili in the Urine of Adults with Acute Urinary Tract Infections," *Infection & Immunity*, 57:1656–62, 1989.

Kuehn, M. J. et al., "P Pili in Uropathogenic *E. coli* are Composite Fibres with Distinct Fibrillar Adhesive Tips," *Nature*, 356:252–5, 1992.

Lin, J.-H. et al., "Precursor Sequence, Processing, and Urothelium-Specific Expression of a Major 15-kDa Protein Subunit of Asymmetric Unit Membrane," *Journal of Biological Chemistry*, 269:1775–84, 1994.

Lin, J.-H, et al., "A Tissue-Specific Promoter That Can Drive a Foreign Gene to Express in the Suprabasal Urothelial Cells of Transgenic Mice," *Proceedings of the National Academy of Sciences of the United States of America*, 92:679–83, 1995.

O'Hanley, P. et al., "Molecular Basis of *Escherichia coli* Colonization of the Upper Urinary Tract in BALB/c Mice. Gal-Gal Pili Immunization Prevents *Escherichia coli* Pyelonephritis in the BALB/c Mouse Model of Human Pyelonephritis," *Journal of Clinical Investigation*, 75:347–60, 1985.

Sauter, S. L. et al., "Identification of the Specific Oligosaccharide Sites Recognized by Type 1 Fimbriae from *Escherichia coli* on Nonspecific Cross-Reacting Antigen, A CD66 Cluster Granulocyte Glycoprotein," *Journal of Biological Chemistry*, 268:15510–6, 1993.

Schaeffer, A. J. et al., "Recurrent Urinary Tract Infection in the Female Patient," [Review], *Urology*, 32 (3 Suppl): 12–15, 1988.

Schaeffer, A. J. et al., "Potential Role of Phase Variation of Type 1 Pili in Urinary Tract Infection and Bacterial Prostatitis," *Infection*, 19 Suppl. 3:S14–149, 1991.

Schaeffer, A. J. et al., "Urinary Tract Infection in Men-State of the Art [See Comments]," [Review], *Infection*, 22 Suppl 1:S19–21, 1994.

Schaeffer, A. J. et al., "Relationship of Type 1 Pilus Expression in *Escherichia coli* to Ascending Urinary Tract Infections in Mice," *Infection & Immunity*, 55:373–80. 1987.

Schoolnik, G. K. et al., "How *Escherichia coli* Infects the Urinary Tract," *The New England Journal of Medicine*, 320:804–805, 1989.

Schoolnik, G. K. et al., "Uropathogenic *Escherichia coli*: Molecular Mechanisms of Adherence," [Review] *Advances in Experimental Medicine & Bioloqy*, 224:53–62, 1987.

Sharon, W. E. et al., "Bacterial Lectins, Cell—Cell Recognition and Infectious Disease," [Review], *Febs Letters*, 217:145–57, 1987.

Sokurenko, E. V. et al., "Functional Heterogeneity of Type 1 Fimbriae of *Escherichia coli*," *Infect. Immun.*, 60:4709–19, 1992.

Sokurenko, E. V. et al., "Quantitative Differences in Adhesiveness of Type 1 Fimbriated *Escherichia coli* due to Structural Differences in fimH Genes," *J. Bacteriol.*, 177:3680–6, 1995.

Sokurenko, E. V. et al., "FimH Family of Type 1 Fimbrial Adhesins: Functional Heterogeneity Due to Minor Sequence Variations Among fimH Genes," *J. Bacteriol.*, 176:748–55, 1994.

Stamm, W. E. et al., "Urinary Tract Infections: From Pathogenesis to Treatment," [Review], *Journal of Infectious Diseases*, 1159:400–6, 1989.

Stromberg, N. et al., "Host-Specificity of Uropathogenic *Escherichia coli* Depends on Differences in Binding Specificity to Gal Alpha 1-4Cal-containing Isoreceptors," *Embo Journal*, 9:2001–10, 1990.

Stromberg, N. et al., "Saccharide Orientation at the Cell Surface Affect Glycolipid Receptor Function," *Proceedings of the National Academy of Sciences of the United States of America*, 88:9340–4, 1991.

Venegas, M. F. et al., "Binding of Type 1-Piliated *Escherichia coli* to Vaginal Mucus," *Infection & Immunity*, 63:416–22, 1995.

Walz et al., "Towards the Molecular Architecture of the Asymmetric Unit Membrane of the Mammalian Urinary Bladder Epithelium: a Closed "Twisted Ribbon" Structure," *Journal of Molecular Bioloqy*, 248:887–900, 1995.

Wu, X-R. et al., "Mammalian Uroplakins. A Group of Highly Conserved Urothelial Differentiation-Related Membrane Proteins," *Journal of Biological Chemistry*, 269:13716–24, 1994.

Wu, X.-R. et al., "Large Scale Purification and Immunolocalization of Bovine Uroplakins I, II, and III, Molecular Markers of Urothelial Differentiation," *Journal of Biological Chemistry*, 265:19170–9, 1990.

Wu, X.-R. et al., "Molecular Cloning of a 47 kDa Tissue-Specific and Differentiation Dependent Urothelial Cell Surface Glycoprotein," *Journal of Cell Science*, 106:31–43, 1993.

Yu, J. et al., "Uroplakins Ia and Ib, Two Major Differentiation Products of Bladder Epithelium, Belong to a Family of Four Transmembrane Domain (4TM) Proteins," *J. Cell Biology*, 125:171–82, 1994.

Yu, J. et al., "Uroplakin I: a 27-kD Protein Associated with the Asymmetrical Unit Membrane of Mammalian Urothelium," *J. Cell Biol.*, 111:1207–16, 1990.

---

What is claimed is:

1. A method for screening and testing compounds useful for treatment of urinary tract infection, comprising:

incubating uroplakin Ia and/or uroplakin Ib with a labeled microorganism expressing type I fimbriae which bind to uroplakin Ia and/or uroplakin Ib, in the presence or absence of a compound to be tested; measuring an amount of labeled microorganism bound to said uroplakin Ia and/or Ib in the presence of said compound relative to in the absence of said compound, whereby the lower the amount of labeled microorganism bound to said uroplakin Ia and/or Ib, the better the inhibition of binding and the more likely that said compound is useful for the treatment of urinary tract infection; and obtaining any compound found likely to be useful for the treatment of urinary tract infection in said measuring step.

2. The method of claim 1, wherein both uroplakin Ia and uroplakin Ib are incubated with a labeled microorganism expressing type I fimbriae which bind to uroplakin Ia and/or uroplakin Ib in the presence of a compound to be tested.

3. The method of claim 2, wherein said uroplakin Ia and uroplakin Ib are provided in the form of purified urothelial plaques.

4. The method of claim 1, wherein the labeled microorganism is selected from the group consisting Salmonella, Klebsiella, Citrobacter, Shigella, Enterobacter, Serratia, Proteus, Morganella, and Providencia.

5. The method of claim 1, wherein the labeled microorganism is labeled with a tag selected from the group consisting of $^{35}$[s]-methionine, an enzyme, biotin, and a fluorescent molecule.

* * * * *

SEQUENCE LISTING

```
(1) GENERAL INFORMATION:

(iii) NUMBER OF SEQUENCES: 20

(2) INFORMATION FOR SEQ ID NO:1:

(i) SEQUENCE CHARACTERISTICS:
         (A) LENGTH: 12 amino acids
         (B) TYPE: amino acid
         (C) STRANDEDNESS: single
         (D) TOPOLOGY: linear (ii) MOLECULE TYPE: peptide (ix) FEATURE:
         (D) OTHER INFORMATION: 'Xaa' in position 1 is Asp or Leu;
             'Xaa' in position 2 is Thr or Glu;
             'Xaa' in position 3 is Phe or Val;
             'Xaa' in position 5 is Ser or Phe;
             'Xaa' in position 6 is Thr or Ala;
             'Xaa' in position 7 is Ser or Asp;
             'Xaa' in position 8 is Ala or Ser;
             'Xaa' in position 9 is Phe or Asn;
             'Xaa' in position 10 is Arg or Gln;
             'Xaa' in position 11 is Ala or Gly; and
             'Xaa' in position 12 is Thr or Ile.

(xi) SEQUENCE DESCRIPTION: SEQ ID NO:1:

Xaa Xaa Xaa Tyr Xaa Xaa Xaa Xaa Xaa Xaa Xaa Xaa
1               5                  10

(2) INFORMATION FOR SEQ ID NO:2:

(i) SEQUENCE CHARACTERISTICS:
         (A) LENGTH: 19 amino acids
         (B) TYPE: amino acid
         (C) STRANDEDNESS: single
         (D) TOPOLOGY: linear (ii) MOLECULE TYPE: peptide (ix) FEATURE:
         (D) OTHER INFORMATION:  'Xaa' in position 1 is Ile or Asp;
             'Xaa' in position 2 is Glu or Trp;
             'Xaa' in position 3 is Gln or Val; and
             'Xaa' in position 7 is Ser or Gly.

(xi) SEQUENCE DESCRIPTION: SEQ ID NO:2:
```

```
Xaa Xaa Xaa Glu Phe Thr Xaa Ala Phe Arg Ala Thr Thr Pro Glu Val
1               5                   10                  15

Val Phe Pro (2) INFORMATION FOR SEQ ID NO:3:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: 'Xaa' in position 1 is Asp or Gln;
            'Xaa' in position 2 is Met or Tyr;
            'Xaa' in position 3 is Leu or Met;
            'Xaa' in position 4 is Val or Thr;
            'Xaa' in position 5 is Phe or Ser;
            'Xaa' in position 6 is Tyr or Asn;
            'Xaa' in position 7 is Ser or Pro;
            'Xaa' in position 8 is Ala or Ser;
            'Xaa' in position 9 is Asp or Leu;
            'Xaa' in position 10 is Ser or Ile;
            'Xaa' in position 11 is Asn or Thr; and
            'Xaa' in position 12 is Gln or Lys.

(xi) SEQUENCE DESCRIPTION: SEQ ID NO:3:

Xaa Xaa Xaa Xaa Xaa Xaa Xaa Xaa Xaa Xaa Xaa Xaa Gly
1               5                   10

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: 'Xaa' in position 1 is Gln or Leu;
            'Xaa' in position 2 is Met or Gly;
            'Xaa' in position 3 is Leu or His;
            'Xaa' in position 4 is Thr or Leu; and
            'Xaa' in position 5 is Phe or Asp.

(xi) SEQUENCE DESCRIPTION: SEQ ID NO:4:

Xaa Xaa Xaa Xaa Xaa Tyr Leu Phe Thr Lys
1               5                   10

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION:  'Xaa' in position 1 is Asp or Ala;
            'Xaa' in position 2 is Lys or Phe;
            'Xaa' in position 4 is Asp or Ile;
            'Xaa' in position 6 is Trp or Thr;
            'Xaa' in position 7 is Val or Leu;
            'Xaa' in position 8 is Arg or Ser;
            'Xaa' in position 10 is Leu or Phe;
            'Xaa' in position 11 is Leu or Gln;
            'Xaa' in position 12 is Ser or Gly;
```

'Xaa' in position 13 is Pro or Leu;
'Xaa' in position 14 is Val or Leu;
'Xaa' in position 15 is Met or Ile;
'Xaa' in position 16 is Phe or Thr;
'Xaa' in position 17 is Gly or Glu;
'Xaa' in position 18 is Asn or Leu; and
'Xaa' in position 20 is Ile or Leu.

(xi) SEQUENCE DESCRIPTION: SEQ ID NO:5:

```
Xaa Xaa Asp Xaa Ser Xaa Xaa Xaa Gly Xaa Xaa Xaa Xaa Xaa Xaa
1               5                   10                  15

Xaa Xaa Val Xaa
            20
```

(2) INFORMATION FOR SEQ ID NO:6:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Asp Glu Val Xaa Phe Thr Ser Ala Phe Arg Ala Thr Thr Pro Glu Val
1               5                   10                  15

Val Phe Pro
```

(2) INFORMATION FOR SEQ ID NO:7:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Leu Thr Phe Tyr Ser Ala Asp Ser Asn Gln Gly Ile
1               5                   10
```

(2) INFORMATION FOR SEQ ID NO:8:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Ile Trp Gln Glu Xaa Xaa Gly
1               5
```

(2) INFORMATION FOR SEQ ID NO:9:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Gln Met Leu Thr Phe Tyr Ser Ala Asp Ser Asn Gln Gly
 1               5                  10
```

(2) INFORMATION FOR SEQ ID NO:10:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Asp Tyr Met Val Ser Asn Pro Ser Leu Ile Thr Lys
 1               5                  10
```

(2) INFORMATION FOR SEQ ID NO:11:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Leu Gly His Leu Asp Tyr Leu Phe Thr Lys
 1               5                  10
```

(2) INFORMATION FOR SEQ ID NO:12:

(i) SEQUENCE CHARACTERISTICS:
        (A) LENGTH: 1365 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 19..792

(xi) SEQUENCE DESCRIPTION: SEQ ID NO:12:

```
GGCAGAGAAG GCAGGACT ATG GCT TCT GCA GCA GCA GCA ACG ACA GAG AAG        51
                    Met Ala Ser Ala Ala Ala Ala Thr Thr Glu Lys
                     1               5                  10

GGG TCT CCA GTT GTG GTG GGT CTG CTG GTC ATG GGC AAC ATC ATT ATT        99
Gly Ser Pro Val Val Val Gly Leu Leu Val Met Gly Asn Ile Ile Ile
             15                  20                  25

CTG CTG TCA GGC CTG GCC CTG TTT GCT GAA ACG GTA TGG GTG ACC GCT       147
Leu Leu Ser Gly Leu Ala Leu Phe Ala Glu Thr Val Trp Val Thr Ala
         30                  35                  40

GAC CAG TAC CGC ATA TAC CCG CTG ATG GGC GTC TCG GGC AAG GAT GAC       195
Asp Gln Tyr Arg Ile Tyr Pro Leu Met Gly Val Ser Gly Lys Asp Asp
     45                  50                  55

GTC TTC GCC GGC GCC TGG ATC GCC ATC TTC TGC GGC TTC TCC TTC TTC       243
Val Phe Ala Gly Ala Trp Ile Ala Ile Phe Cys Gly Phe Ser Phe Phe
 60                  65                  70                  75

GTG GTG GCC AGC TTT GGT GTG GGC GCA GCA CTC TGC CGC CGC CGC TCC       291
Val Val Ala Ser Phe Gly Val Gly Ala Ala Leu Cys Arg Arg Arg Ser
                 80                  85                  90

ATG ATC CTC ACG TAC CTG ATA CTC ATG CTC ATC ATC TAC ATC TTT GAG       339
Met Ile Leu Thr Tyr Leu Ile Leu Met Leu Ile Ile Tyr Ile Phe Glu
             95                 100                 105
```

```
TGC GCC TCC TGC ATC ACG TCC TAC ACC CAC CGA GAC TAT ATG GTG TCC      387
Cys Ala Ser Cys Ile Thr Ser Tyr Thr His Arg Asp Tyr Met Val Ser
        110                 115                 120

AAC CCG TCC CTG ATC ACC AAG CAG ATG TTG ACA TTC TAT AGT GCA GAC      435
Asn Pro Ser Leu Ile Thr Lys Gln Met Leu Thr Phe Tyr Ser Ala Asp
125                 130                 135

TCG AAC CAG GGC CGG GAA CTG ACC CGC CTC TGG GAT CGC ATC ATG ATT      483
Ser Asn Gln Gly Arg Glu Leu Thr Arg Leu Trp Asp Arg Ile Met Ile
140                 145                 150                 155

GAG CAA GAG TGC TGT GGC ACG TCA GGC CCC ATG GAC TGG GTG AAC TTC      531
Glu Gln Glu Cys Cys Gly Thr Ser Gly Pro Met Asp Trp Val Asn Phe
                160                 165                 170

ACG TCT GCC TTC CGG GCC ACC ACC CCA GAG GTG GTG TTC CCC TGG CCC      579
Thr Ser Ala Phe Arg Ala Thr Thr Pro Glu Val Val Phe Pro Trp Pro
            175                 180                 185

CCG CTA TGC TGT CGA CGG ACC GGC AAC TTC ATC CCA GTC AAT GAA GAA      627
Pro Leu Cys Cys Arg Arg Thr Gly Asn Phe Ile Pro Val Asn Glu Glu
            190                 195                 200

GGC TGC CGC CTG GGC CAC CTG GAC TAC CTG TTC ACC AAG GGC TGC TTT      675
Gly Cys Arg Leu Gly His Leu Asp Tyr Leu Phe Thr Lys Gly Cys Phe
        205                 210                 215

GAA CAT ATT GGC CAC GCC ATC GAC AGC TAC ACG TGG GGC ATC TCG TGG      723
Glu His Ile Gly His Ala Ile Asp Ser Tyr Thr Trp Gly Ile Ser Trp
220                 225                 230                 235

TTT GGG TTT GCC ATC CTG ATG TGG ACG CTC CCC GTG ATG CTG ATA GCC      771
Phe Gly Phe Ala Ile Leu Met Trp Thr Leu Pro Val Met Leu Ile Ala
                240                 245                 250

ATG TAT TTC TAC ACC ACG TTG TGAGAACGAG AAGTGAAGGC CACGTGCACA         822
Met Tyr Phe Tyr Thr Thr Leu
                255

CCTGGCTTCC TCCTCCTCCT GCTCTGGCTT CCTCTGGCTG AGATGGCCGA CTCGCCTCTC    882

CCTGTCCCAC CTCCCTGGCC CAGTCCTCCC TCCACTCCAA AGATGTTTTA CCAGGTTTCT    942

GAGCCCCTGC TGAGAGTCGG GGTGCCCTAA AACCCCTGGA CATCCTCTTA CTAAGGACTA   1002

AGCTTCCAGC AAATTCTCTA AGGGGTGTGT AGCATGTGTG TACAGACCGT TAGTCCTTAA   1062

CCTCCTTTCA CTAGACTGAT TCTTGGCCCA TCTTTCAGGG TCAACTTCAA GTCCTGTCCT   1122

CGGGGGGGCC CTTTCCTGAT CTCACCACCC CATTCACAGA TGCCTTTCTT ATAGTTCCCA   1182

GAGCTCCTCC TCCATGGTGG ATGTCATCAT CATCACTGAA TAGTTTGTGA TTGTCTGTTT   1242

AAATTCTGGT AGAACTGGGA TTGCCATGAG GAGAGGGACA AGTTCTGTTA TGGTCACTTT   1302

AACATCCCTG CATCACCTGG CATGGGCTGA GCACGGACA TTCAATAAAT ACTACTTGAA    1362

TGA                                                                 1365

(2) INFORMATION FOR SEQ ID NO:13:

(i) SEQUENCE CHARACTERISTICS:
        (A) LENGTH: 258 amino acids
        (B) TYPE: amino acid
        (D) TOPOLOGY: linear (ii) MOLECULE TYPE: protein (xi) SEQUENCE DESCRIPTION: SEQ ID NO:13:

Met Ala Ser Ala Ala Ala Thr Thr Glu Lys Gly Ser Pro Val Val
1               5                   10                  15

Val Gly Leu Leu Val Met Gly Asn Ile Ile Ile Leu Leu Ser Gly Leu
            20                  25                  30
```

-continued

```
Ala Leu Phe Ala Glu Thr Val Trp Val Thr Ala Asp Gln Tyr Arg Ile
         35                  40                  45

Tyr Pro Leu Met Gly Val Ser Gly Lys Asp Asp Val Phe Ala Gly Ala
     50                  55                  60

Trp Ile Ala Ile Phe Cys Gly Phe Ser Phe Phe Val Val Ala Ser Phe
 65              70                  75                  80

Gly Val Gly Ala Ala Leu Cys Arg Arg Arg Ser Met Ile Leu Thr Tyr
                 85                  90                  95

Leu Ile Leu Met Leu Ile Ile Tyr Ile Phe Glu Cys Ala Ser Cys Ile
            100                 105                 110

Thr Ser Tyr Thr His Arg Asp Tyr Met Val Ser Asn Pro Ser Leu Ile
            115                 120                 125

Thr Lys Gln Met Leu Thr Phe Tyr Ser Ala Asp Ser Asn Gln Gly Arg
            130                 135                 140

Glu Leu Thr Arg Leu Trp Asp Arg Ile Met Ile Glu Gln Glu Cys Cys
145                 150                 155                 160

Gly Thr Ser Gly Pro Met Asp Trp Val Asn Phe Thr Ser Ala Phe Arg
                165                 170                 175

Ala Thr Thr Pro Glu Val Val Phe Pro Trp Pro Leu Cys Cys Arg
            180                 185                 190

Arg Thr Gly Asn Phe Ile Pro Val Asn Glu Glu Gly Cys Arg Leu Gly
            195                 200                 205

His Leu Asp Tyr Leu Phe Thr Lys Gly Cys Phe Glu His Ile Gly His
    210                 215                 220

Ala Ile Asp Ser Tyr Thr Trp Gly Ile Ser Trp Phe Gly Phe Ala Ile
225                 230                 235                 240

Leu Met Trp Thr Leu Pro Val Met Leu Ile Ala Met Tyr Phe Tyr Thr
                245                 250                 255

Thr Leu (2) INFORMATION FOR SEQ ID NO:14:

(i) SEQUENCE CHARACTERISTICS:
        (A) LENGTH: 1966 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 62..841

(xi) SEQUENCE DESCRIPTION: SEQ ID NO:14:

GCGTGCAGAG AGCCGACACA GTACCAGGAG GAGGAGGAGA GGCTTGGGGG AAATCCTGAA          60

G ATG GCC AAA GAC GAC TCC ACT GTT CGT TGC TTC CAG GGC CTG CTG            106
  Met Ala Lys Asp Asp Ser Thr Val Arg Cys Phe Gln Gly Leu Leu
  1               5                   10                  15

ATT TTT GGA AAT GTG ATT ATC GGT ATG TGC AGC ATC GCC CTG ATG GCA          154
Ile Phe Gly Asn Val Ile Ile Gly Met Cys Ser Ile Ala Leu Met Ala
                20                  25                  30

GAG TGC ATC TTC TTT GTA TCA GAC CAA AAC AGC CTC TAC CCA CTG CTT          202
Glu Cys Ile Phe Phe Val Ser Asp Gln Asn Ser Leu Tyr Pro Leu Leu
            35                  40                  45

GAA GCC ACC AAC AAT GAC GAC ATC TAT GCG GCA GCC TGG ATT GGC ATG          250
Glu Ala Thr Asn Asn Asp Asp Ile Tyr Ala Ala Ala Trp Ile Gly Met
        50                  55                  60
```

```
TCT GTT GGC ATC TGC CTC TTC TGC CTC TCT GTC CTG GGC ATC GTA GGC      298
Ser Val Gly Ile Cys Leu Phe Cys Leu Ser Val Leu Gly Ile Val Gly
 65                  70                  75

ATC ATG AAG TCC AAC AGG AAA ATT CTT CTG GTG TAT TTC ATC CTG ATG      346
Ile Met Lys Ser Asn Arg Lys Ile Leu Leu Val Tyr Phe Ile Leu Met
 80                  85                  90                  95

TTT ATT GTA TAT GCT TTT GAA GTG GCA TCT TGT ATC ACA GCA GCA ACA      394
Phe Ile Val Tyr Ala Phe Glu Val Ala Ser Cys Ile Thr Ala Ala Thr
                    100                 105                 110

CAA CGA GAC TTT TTC ACA CCC AAC CTC TTC CTG AAG CAG ATG CTG GAG      442
Gln Arg Asp Phe Phe Thr Pro Asn Leu Phe Leu Lys Gln Met Leu Glu
                115                 120                 125

AGA TAC CAA AAC AAC AGT CCT CCA AAC AAT GAT GAC CAA TGG AAA AAC      490
Arg Tyr Gln Asn Asn Ser Pro Pro Asn Asn Asp Asp Gln Trp Lys Asn
            130                 135                 140

AAT GGA GTC ACC AAG ACC TGG GAC AGA CTT ATG CTC CAG GAC AAT TGC      538
Asn Gly Val Thr Lys Thr Trp Asp Arg Leu Met Leu Gln Asp Asn Cys
        145                 150                 155

TGT GGT GTA AAT GGC CCG TCA GAC TGG CAG AAA TAC ACC TCT GCC TTC      586
Cys Gly Val Asn Gly Pro Ser Asp Trp Gln Lys Tyr Thr Ser Ala Phe
160                 165                 170                 175

CGG ACT GAG AAC AGC GAT GCT GAC TAC CCC TGG CCT CGT CAA TGC TGT      634
Arg Thr Glu Asn Ser Asp Ala Asp Tyr Pro Trp Pro Arg Gln Cys Cys
                180                 185                 190

GTT ATG AAC AGC CTT AAA GAA CCT CTC AAC CTG GAC GCC TGC AAA TTA      682
Val Met Asn Ser Leu Lys Glu Pro Leu Asn Leu Asp Ala Cys Lys Leu
                195                 200                 205

GGA GTG CCT GGA TAC TAC CAT AGT CAT GGC TGC TAT GAG CTG ATC TCT      730
Gly Val Pro Gly Tyr Tyr His Ser His Gly Cys Tyr Glu Leu Ile Ser
            210                 215                 220

GGA CCA ATG AAC CGA CAT GCC TGG GGA GTT GCA TGG TTT GGA TTT GCC      778
Gly Pro Met Asn Arg His Ala Trp Gly Val Ala Trp Phe Gly Phe Ala
        225                 230                 235

ATT CTC TGT TGG ACT TTC TGG GTT CTC CTG GGT ACC ATG TTC TAC TGG      826
Ile Leu Cys Trp Thr Phe Trp Val Leu Leu Gly Thr Met Phe Tyr Trp
240                 245                 250                 255

AGC AGA ATT GAC TAT TAAGAATGAA GTGTATGCAC CATACCACTC CCCACAGTGA      881
Ser Arg Ile Asp Tyr
                260

CTTTGGATTT GGTGCTGGAA ATGCTGTCTC CTAATGTTCT ACCTTTGTGC TGCCCGGGAA    941

CTTACGCATT CTTCCTACAT TGCCAAGTAC GTTGGTATGG GGTTCCTTTA AGCTCTCAGA   1001

CTCTGAAATT TTCAGCACAT GTGTTTTCAC CCTGATCTAG GATTCTGCAA CATTGTTATA   1061

GACTGTAGGA AAGGGAGGAT TTAGGATAGT AGATAATAAC TATTCCCATC TTTGTTATT    1121

TTTAATGTGG GGGCATAAAG ACATTCCTAG GAACCTGTGT TATACTGCAA GCCAAGTCTG   1181

TATTGGGACA GCAAATCTGC CTGTATTTCT CACTGCTTTC TAAAAGTACC CTGATGGCAC   1241

CCCACTCCAG TACTCTTGCC TGGAAAATCC CATGGACGGA GGAGCCTGAT GGGCTGCAGT   1301

CCATGGGGTC GCAAAGAGTC GGACCCGACT GGGCGACTTC ACTTTCACTT TTCACTTTCA   1361

TGCATTGGAG AAGGAAATGG CAACCCACTC CAGTGTTCTT GCCTGGAGAA TCCCAGGGAT   1421

GGAGGAGCCT GGAGGGCTGC CGTCTATGGG GTCACACAGA GTCGGACACG ACTGAAGCGA   1481

CTTAGCAGCA GCAGCAGCAA AGGCTTTCAT TGTATCAGTA TTGTCCCAGT GAGAGAACTA   1541

AGGAGAAGAC TGCTGAAACA TCTTTTGAAT TTGTTCTATG GTGGCTCCCA CCTACAGACT   1601

CAAGTGATTC TCTTAAAGCT AGCTTGGGAA CCCTTTATTA TCCAAGACAA GGCCTGATCT   1661

TGAACAAACA GTGGTTGAAA TTTCCTCTCA GACACTGCAG AGTAATTCAT GCTGGTAACC   1721
```

```
TCAATTCTCC CACTAATTAA AAGTACGTGA ACTTTTGGGA CAAAGGAGAG ACCTGTTACA    1781

CATTTACCAC CTTCAACCTA AAACTGCTTT CCAACAGGGA AGAAGCAAGC CAGCTGTTAC    1841

TTAGGTGATT TAGGGTGATC TGTGCACTGC AAAATATTTT TCTTCTGATC TGTTTCCTTT    1901

TGTGATCCTG AAGGAATTTC TTATAACAAC ATTTGTCTTT ATATAAATAA AGAGAGTTTT    1961

AAATA                                                                1966
```

(2) INFORMATION FOR SEQ ID NO:15:

(i) SEQUENCE CHARACTERISTICS:
        (A) LENGTH: 260 amino acids
        (B) TYPE: amino acid
        (D) TOPOLOGY: linear (ii) MOLECULE TYPE: protein (xi) SEQUENCE DESCRIPTION: SEQ ID NO:15:

```
Met Ala Lys Asp Asp Ser Thr Val Arg Cys Phe Gln Gly Leu Leu Ile
 1               5                  10                  15

Phe Gly Asn Val Ile Ile Gly Met Cys Ser Ile Ala Leu Met Ala Glu
            20                  25                  30

Cys Ile Phe Phe Val Ser Asp Gln Asn Ser Leu Tyr Pro Leu Leu Glu
        35                  40                  45

Ala Thr Asn Asn Asp Asp Ile Tyr Ala Ala Ala Trp Ile Gly Met Ser
    50                  55                  60

Val Gly Ile Cys Leu Phe Cys Leu Ser Val Leu Gly Ile Val Gly Ile
65                  70                  75                  80

Met Lys Ser Asn Arg Lys Ile Leu Leu Val Tyr Phe Ile Leu Met Phe
                85                  90                  95

Ile Val Tyr Ala Phe Glu Val Ala Ser Cys Ile Thr Ala Ala Thr Gln
            100                 105                 110

Arg Asp Phe Phe Thr Pro Asn Leu Phe Leu Lys Gln Met Leu Glu Arg
        115                 120                 125

Tyr Gln Asn Asn Ser Pro Pro Asn Asn Asp Asp Gln Trp Lys Asn Asn
    130                 135                 140

Gly Val Thr Lys Thr Trp Asp Arg Leu Met Leu Gln Asp Asn Cys Cys
145                 150                 155                 160

Gly Val Asn Gly Pro Ser Asp Trp Gln Lys Tyr Thr Ser Ala Phe Arg
                165                 170                 175

Thr Glu Asn Ser Asp Ala Asp Tyr Pro Trp Pro Arg Gln Cys Cys Val
            180                 185                 190

Met Asn Ser Leu Lys Glu Pro Leu Asn Leu Asp Ala Cys Lys Leu Gly
        195                 200                 205

Val Pro Gly Tyr Tyr His Ser His Gly Cys Tyr Glu Leu Ile Ser Gly
    210                 215                 220

Pro Met Asn Arg His Ala Trp Gly Val Ala Trp Phe Gly Phe Ala Ile
225                 230                 235                 240

Leu Cys Trp Thr Phe Trp Val Leu Leu Gly Thr Met Phe Tyr Trp Ser
                245                 250                 255

Arg Ile Asp Tyr
            260
```

(2) INFORMATION FOR SEQ ID NO:16:

(i) SEQUENCE CHARACTERISTICS:
        (A) LENGTH: 18 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:16:

Ala Lys Asp Asp Ser Thr Val Arg Ser Phe Gln Gly Leu Leu Ile Phe
1               5                   10                  15

Gly Asn (2) INFORMATION FOR SEQ ID NO:17:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Glu Leu Val Ser Val Val Asp Ser Gly Ser Gly
1               5                   10

(2) INFORMATION FOR SEQ ID NO:18:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Asp Ser Gly Ser Gly Phe Thr Val Thr Arg Leu Ser Ala
1               5                   10

(2) INFORMATION FOR SEQ ID NO:19:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Ser Ala Tyr Gln Val Thr Asn Leu Ala Pro Gly Thr Lys Tyr Tyr Ile
1               5                   10                  15

(2) INFORMATION FOR SEQ ID NO:20:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Gly Ala Ser Thr Glu Ser Ser Arg Glu Ile Pro Met Ser Thr Phe Pro
1               5                   10                  15

Arg Arg Lys